(12) United States Patent
Bodwell

(10) Patent No.: US 12,226,580 B2
(45) Date of Patent: *Feb. 18, 2025

(54) BIFURCATED CANNULA DEVICE

(71) Applicant: Vapotherm, Inc., Exeter, NH (US)

(72) Inventor: Jesse Bodwell, Manchester, NH (US)

(73) Assignee: VAPOTHERM, INC., Exeter, NH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/214,740

(22) Filed: Jun. 27, 2023

(65) Prior Publication Data
US 2024/0165358 A1    May 23, 2024

Related U.S. Application Data

(63) Continuation of application No. 16/124,818, filed on Sep. 7, 2018, now Pat. No. 11,724,056.
(Continued)

(51) Int. Cl.
*A61M 16/06* (2006.01)
*A61M 11/00* (2006.01)
(Continued)

(52) U.S. Cl.
CPC .... *A61M 16/0672* (2014.02); *A61M 16/0666* (2013.01); *A61M 16/0816* (2013.01);
(Continued)

(58) Field of Classification Search
CPC .......... A61M 16/0672; A61M 16/0666; A61M 16/0816; A61M 11/00; A61M 16/0683;
(Continued)

(56) References Cited

U.S. PATENT DOCUMENTS

RE24,534 E   9/1958   Dahl
2,941,544 A  6/1960   Lucien
(Continued)

FOREIGN PATENT DOCUMENTS

AU   2013212314   11/2017
AU   2013337995    6/2018
(Continued)

OTHER PUBLICATIONS

International Search Report and Written Opinion for PCT/US2016/040465 dated Oct. 4, 2016 (16 pages).
(Continued)

*Primary Examiner* — Timothy A Stanis
*Assistant Examiner* — Tina Zhang
(74) *Attorney, Agent, or Firm* — McDermott Will & Emery LLP

(57) ABSTRACT

Devices and methods for providing respiratory therapy are disclosed. One device includes a first lumen, a second lumen, and a bridge with at least one opening. The first lumen has a first inlet end to receive a first flow of breathing gas, a first outlet end to deliver the first flow, and a first bend between the first inlet end and the first outlet end. The second lumen has a second inlet end to receive a second flow of breathing gas, a second outlet end to deliver the second flow, and a second bend between the second inlet end and the second outlet end. The bridge separates the first lumen and the second lumen, attaches to the first lumen at the first bend and the second lumen at the second bend, and is configured to maintain the first flow of breathing gas separate from the second flow of breathing gas.

9 Claims, 13 Drawing Sheets

Related U.S. Application Data

(60) Provisional application No. 62/555,945, filed on Sep. 8, 2017.

(51) Int. Cl.
| | |
|---|---|
| *A61M 16/08* | (2006.01) |
| *A61M 16/16* | (2006.01) |
| A61M 16/10 | (2006.01) |
| A61M 16/14 | (2006.01) |
| B29C 41/00 | (2006.01) |
| B29C 41/14 | (2006.01) |

(52) U.S. Cl.
CPC ......... *A61M 11/00* (2013.01); *A61M 16/0683* (2013.01); *A61M 16/0875* (2013.01); *A61M 16/1075* (2013.01); *A61M 16/14* (2013.01); *A61M 16/16* (2013.01); *A61M 2207/00* (2013.01); *A61M 2207/10* (2013.01); *A61M 2209/088* (2013.01); *A61M 2230/42* (2013.01); *B29C 41/00* (2013.01); *B29C 41/14* (2013.01)

(58) Field of Classification Search
CPC .......... A61M 16/0875; A61M 16/1075; A61M 16/14; A61M 16/16; A61M 2207/00; A61M 2207/10; A61M 2209/088; A61M 2230/42; A61M 15/08; B29C 41/00; B29C 41/14

See application file for complete search history.

(56) References Cited

U.S. PATENT DOCUMENTS

| | | | |
|---|---|---|---|
| 4,003,398 A | 1/1977 | Duveau | |
| 4,422,456 A | 12/1983 | Tiep | |
| 4,708,166 A | 11/1987 | Kobold | |
| 4,782,832 A | 11/1988 | Trimble | |
| 4,790,308 A | 12/1988 | Weichselbuam | |
| 5,099,836 A | 3/1992 | Rowland | |
| 5,113,911 A | 5/1992 | Hirsh | |
| 5,433,242 A | 7/1995 | Buchtel | |
| 5,645,539 A * | 7/1997 | Solomon | A61M 16/0825 604/905 |
| 6,561,188 B1 | 5/2003 | Ellis | |
| 6,805,126 B2 | 10/2004 | Dutkiewicz | |
| 6,986,353 B2 | 1/2006 | Wright | |
| 7,007,694 B2 | 3/2006 | Aylsworth et al. | |
| 7,481,244 B2 | 1/2009 | Bivin | |
| 7,662,181 B2 | 2/2010 | Deem | |
| 7,743,770 B2 | 6/2010 | Curti | |
| 7,832,400 B2 | 11/2010 | Curti et al. | |
| 8,631,799 B2 * | 1/2014 | Davenport | A61M 16/1095 128/207.14 |
| 9,333,317 B2 | 5/2016 | Cortez et al. | |
| 9,597,263 B2 | 3/2017 | Visveshwara | |
| 9,822,515 B2 | 11/2017 | Wu | |
| 9,925,348 B2 | 3/2018 | Payton et al. | |
| 10,100,622 B2 | 10/2018 | Gonzalez | |
| 10,265,494 B2 | 4/2019 | Cortez, Jr. et al. | |
| 10,300,236 B2 | 5/2019 | Cortez, Jr. et al. | |
| 2004/0112383 A1 | 6/2004 | Curti | |
| 2004/0226566 A1 | 11/2004 | Gunaratnam et al. | |
| 2005/0028822 A1 | 2/2005 | Sleeper et al. | |
| 2005/0066976 A1 * | 3/2005 | Wondka | A61M 16/0605 128/207.18 |
| 2005/0103347 A1 | 5/2005 | Curti et al. | |
| 2005/0229927 A1 | 10/2005 | Fink et al. | |
| 2005/0229928 A1 | 10/2005 | Irvi | |
| 2006/0030696 A1 | 2/2006 | Bonnerjea | |
| 2006/0180151 A1 | 8/2006 | Rinaldi | |
| 2006/0230929 A1 | 10/2006 | Bliss | |
| 2006/0230931 A1 | 10/2006 | Bliss | |
| 2007/0175473 A1 | 8/2007 | Lewis et al. | |
| 2008/0121230 A1 | 5/2008 | Cortez et al. | |
| 2008/0223375 A1 | 9/2008 | Cortez, Jr. et al. | |
| 2009/0044808 A1 | 2/2009 | Guney | |
| 2009/0101147 A1 | 4/2009 | Landis | |
| 2009/0250132 A1 | 10/2009 | Bivin | |
| 2009/0253995 A1 | 10/2009 | Lewis et al. | |
| 2010/0096019 A1 | 4/2010 | DiPerna | |
| 2010/0108073 A1 | 5/2010 | Zollinger et al. | |
| 2010/0113955 A1 | 5/2010 | Colman | |
| 2010/0252037 A1 | 10/2010 | Wondka | |
| 2010/0282247 A1 | 11/2010 | Kadrichu | |
| 2011/0067704 A1 | 3/2011 | Kooij et al. | |
| 2011/0073116 A1 | 3/2011 | Genger | |
| 2011/0094518 A1 | 4/2011 | Cipollone | |
| 2011/0146685 A1 | 6/2011 | Allan et al. | |
| 2011/0232649 A1 | 9/2011 | Collazo et al. | |
| 2011/0270166 A1 | 11/2011 | Martin | |
| 2011/0284001 A1 | 11/2011 | Tero | |
| 2012/0090622 A1 | 4/2012 | Chang | |
| 2012/0125332 A1 | 5/2012 | Niland | |
| 2012/0167878 A1 | 7/2012 | Belson | |
| 2012/0304992 A1 | 12/2012 | Ratto | |
| 2012/0304999 A1 | 12/2012 | Swift | |
| 2013/0008447 A1 | 1/2013 | Gunaratnam et al. | |
| 2013/0092165 A1 | 4/2013 | Wondka | |
| 2013/0146064 A1 | 6/2013 | Dryden | |
| 2013/0152925 A1 | 6/2013 | Rahmel et al. | |
| 2013/0160772 A1 | 6/2013 | Tabrizchi | |
| 2013/0186395 A1 | 7/2013 | Cortez, Jr. et al. | |
| 2013/0230674 A1 | 9/2013 | Curti | |
| 2014/0066801 A1 | 3/2014 | Tero | |
| 2014/0094669 A1 | 4/2014 | Jaffe | |
| 2014/0116447 A1 | 5/2014 | Cortez, Jr. et al. | |
| 2014/0137744 A1 | 5/2014 | Wilkinson | |
| 2014/0147506 A1 | 5/2014 | Longest et al. | |
| 2014/0150789 A1 | 6/2014 | Flanagan et al. | |
| 2014/0158127 A1 * | 6/2014 | Boucher | A61M 11/00 128/203.22 |
| 2014/0166009 A1 | 6/2014 | Flanagan et al. | |
| 2014/0230942 A1 | 8/2014 | Takai | |
| 2014/0261704 A1 | 9/2014 | Hoogenakker | |
| 2014/0366885 A1 | 12/2014 | Haibach | |
| 2015/0000654 A1 | 1/2015 | Martin | |
| 2015/0000659 A1 | 1/2015 | Martin | |
| 2015/0000660 A1 | 1/2015 | Martin | |
| 2015/0090255 A1 | 4/2015 | Gulliver | |
| 2015/0230731 A1 | 8/2015 | Levitsky | |
| 2016/0015296 A1 | 1/2016 | Garaycochea | |
| 2016/0015921 A1 | 1/2016 | Harrison | |
| 2016/0030696 A1 | 2/2016 | Klenner | |
| 2016/0158476 A1 | 6/2016 | Tatkov | |
| 2016/0271353 A1 | 9/2016 | Cheung | |
| 2017/0000965 A1 | 1/2017 | Cortez et al. | |
| 2017/0348500 A1 | 12/2017 | Johnson | |
| 2018/0064898 A1 | 3/2018 | Evans | |
| 2019/0328990 A1 | 10/2019 | Cortez et al. | |
| 2019/0328993 A1 | 10/2019 | Cortez et al. | |

FOREIGN PATENT DOCUMENTS

| | | | |
|---|---|---|---|
| AU | 2017251790 | 3/2020 | |
| EP | 2022528 | 2/2009 | |
| EP | 2247331 | 11/2010 | |
| EP | 2806926 | 5/2017 | |
| EP | 2914322 | 12/2018 | |
| EP | 3646913 | 5/2020 | |
| EP | 3216475 | 7/2020 | |
| EP | 3747488 | 12/2020 | |
| FR | 2827778 A1 | 1/2003 | |
| JP | 2018089139 | 5/2018 | |
| JP | 2018089139 A * | 6/2018 | ........ A61M 16/0666 |
| WO | WO-9818513 | 5/1998 | |
| WO | WO-2006138579 | 12/2006 | |
| WO | WO-2008060587 | 5/2008 | |
| WO | WO2009094532 | 7/2009 | |
| WO | WO-2013041996 | 3/2013 | |
| WO | WO-2013042004 | 3/2013 | |
| WO | WO-2013112545 | 8/2013 | |
| WO | WO-2013157960 | 10/2013 | |
| WO | WO-2014070833 | 5/2014 | |

(56) References Cited

FOREIGN PATENT DOCUMENTS

| WO | WO-2014142681 | 9/2014 |
| WO | WO-2015121815 | 8/2015 |
| WO | WO-2015164921 | 11/2015 |
| WO | WO-2016043607 | 3/2016 |
| WO | WO-2017062677 | 4/2017 |
| WO | WO-2018005851 | 1/2018 |
| WO | WO-2018065588 | 4/2018 |
| WO | WO-2018068085 | 4/2018 |
| WO | WO-2019191814 | 10/2019 |

OTHER PUBLICATIONS

International Search Report and Written Opinion for PCT/US2017/040079 dated Oct. 18, 2017 (21 pages).
International Search Report and Written Opinion for PCTUS2018/049979 dated Nov. 23, 21018 (16 pages).
International Search Report and Written Opinion for PCT/US2020/039641 dated Oct. 7, 2020 (13 pages).
International Search Report and Written Opinion for PCT/US2021/051987 dated Jan. 5, 2022 (19 pages).
Doshi et al., "High-Velocity Nasal Insufflation in the Treatment of Respiratory Failure: A Randomized Clinical Trial", Annals of Emergency Medicine, Jul. 2017;72(1):73-83.
Spivey S., et al., "Assessment of High Flow Nasal Cannula Therapy use in the Emergency Department Setting: Observations of Practice Across Four Systems", Respiratory Therapy, vol. 10, No. 1, pp. 30-34 (2015).
RBC Aerospace Bearings, "Plain Bearings", Spec Sheet, 2016, p. 43 (107 pgs) (2016).

\* cited by examiner

BIFURCATED CANNULA DEVICE

CROSS-REFERENCE TO RELATED APPLICATIONS

This application is a continuation of U.S. application Ser. No. 16/124,818 filed Sep. 7, 2018 (now U.S. Pat. No. 11,724,056) which claims priority to and benefit of U.S. provisional patent application No. 62/555,945, filed Sep. 8, 2017 (expired), each of which is entirely incorporated herein by reference.

BACKGROUND

Patients with respiratory ailments may be treated with respiratory assist devices, such as devices that deliver supplemental breathing gas to a patient. Such devices may deliver gas to a patient using high flow therapy ("HFT"). HFT devices deliver a high flow rate of breathing gas to a patient via an interface such as a nasal cannula to increase a patient's fraction of inspired oxygen (FiO2) and/or help to facilitate a patient's breathing. Nasal cannulas are commonly used in acute short-term therapy and in therapy for chronic issues. A nasal cannula typically includes one or more nasal prongs, with each prong inserted into a respective nostril during use. A tube or other surface may span the space between the two prongs and rest against the users face. However, rigid materials spanning the space between the two prongs may be uncomfortable to patients. Certain geometries may additionally allow the cannula nosepiece to roll outward, away from patients' faces.

Previously, bifurcated nasal cannulas were dip molded by closely locating a left-side mandrel and a right-side mandrel, leaving a small gap to fill with liquid plastic, forming a rib connecting the two halves of the part and sealing off the gas path, as shown in FIG. 1. Dip molding is a process in which a flexible material is formed over a die by dipping the die into liquid material. The die is removed from the liquid material and heated to cure the liquid material into a solid form. The solid material is flexible which enables it to be stripped or pulled off the die or mandrel. This method of creating bifurcated cannulas results in an oddly shaped gas path with a large empty volume between inlet and outlet ends, as shown in FIG. 2. This empty volume provides a place for condensation to collect (also known as "rainout"). Once the condensation reaches a critical mass in a tube, a liquid droplet or bolus can form and may be delivered to the patient. This can be uncomfortable and, in some cases, dangerous to the patient.

The connecting rib, such as rib 214 of FIG. 2, results in sharp corners where the two mandrels were held in close proximity during dip molding, which causes eddies and high resistance in the gas flow path. Steps or other uneven surfaces in gas flow path geometry, such as those shown in FIG. 2, may trap moisture, causing condensation droplets to increase in size and become noticeable rainout. Additionally, air trapped in eddies has a longer holdup time and therefore better chance to cool in the gas path. Drops in gas temperature greatly contribute to the formation of rainout, because the capacity for air to hold water vapor decreases with a decrease in temperature. Gas paths with high flow resistance are undesirable, especially in high flow therapy, as high flow resistance reduces the amount of flow that can be pushed by a given flow generating device, such as a fan or blower. High flow resistance may cause drops in flow pressure and excessive noise. Furthermore, the connecting rib causes the material to be locally stiff at the rib (when compared to the rest of the cannula). The orientation of the connecting rib that spans the space between the two nasal prongs contacts the skin on the upper lip, which can cause patient discomfort due to the stiff material.

SUMMARY

Disclosed herein are approaches for addressing various of the problems and shortcomings of the state of the art, as identified above. More particularly, disclosed herein are systems, methods, and devices providing a bifurcated nasal cannula with low flow resistance and increased patient comfort. The cannula includes a nosepiece for respiratory therapy having a custom bridge between nasal prongs of the nasal cannula and a smooth bore gas path. The nosepiece may be manufactured by dip molding at least three mandrels fixedly arranged around each other. The three mandrel method allows for design freedom and an open geometry of the nasal bridge. Sacrificial material may be molded completely around the third mandrel and then trimmed and discarded after manufacture. The relatively low monetary cost of the dip molding material allows for discarding the excess material without significantly affecting the production cost. The dip molding process also allows for manufacture of the custom bridge to separate the nasal prongs and but with one or more custom openings that optionally allow for fluid communication with the prongs or between them.

The nosepiece can be provided in several nonlimiting aspects. In one aspect, the nosepiece comprises a first lumen, a second lumen, and a bridge. The first and second lumens deliver breathing gas to the patient when connected to a source of breathing gas, while the bridge spatially, and in some cases fluidically, separates the two lumens. The bridge also provides a surface to rest on the patient's philtrum. The nosepiece provides smoother gas paths than devices in the current state of the art, resulting in low flow resistance, quiet operation, and improved patient comfort.

In some implementations, the first lumen comprises a first inlet end to receive a first flow of breathing gas from a source of breathing gas (for example humidified oxygen or air), and a first outlet end through which the first flow is delivered. The second lumen comprises a second inlet end to receive a second flow of breathing gas from a source of breathing gas, and a second outlet end through which the second flow is delivered. The bridge may be hollow and have at least one opening, for example to provide a connection to a medicament delivery device to the nosepiece. The bridge may fluidically seal the two lumens from each other. For example, the bridge may attach a nebulizer to the nosepiece. The nebulizer may provide a third outlet end, through which the medicament is delivered. Alternatively, the bridge may comprise a plurality of openings configured to allow medicament to flow from an attached medicament delivery device, such as a nebulizer, to the first and second lumens. For example, these openings may allow aerosolized medicament from a nebulizer to join the first and second breathing gas flows through a slipstream effect.

Numerous examples are available for adapting and implementing the nosepieces. Those include any of the features, aspects and examples recited herein. For example, the first lumen may comprise a first bend between the first inlet end and the first outlet end. The second lumen may comprise a second bend between the second inlet end and the second outlet end. The bridge may attach to the outer surface of the first lumen at the first bend and the outer surface of the second lumen at the second bend. In an example, the bridge may form a fluid barrier between the first lumen and the second lumen, so the two lumens are fluidically sealed from each other. In another example, the bridge may be configured to allow fluid communication between the first flow and the second flow. For instance, the bridge may be configured with small flow channels or membranes that permit flow, osmosis, or any other suitable fluid communication between the lumens and the bridge.

The lumens may also be shaped and arranged in structures that facilitate a smooth flow. The output gas flow velocity may be adjusted to suit patient needs by adjusting the internal diameter at the first and second outlet ends. In an embodiment, an internal diameter of the first lumen tapers toward the first outlet end, and an internal diameter of the second lumen tapers toward the second outlet end. Such a taper increases output gas flow velocity at the first and second outlet ends.

In another embodiment, the first lumen may have a constant internal diameter and the second lumen may have a constant internal diameter. The internal diameters of the first and second lumens may be the same or different.

In some embodiments, an internal diameter of the first inlet end may be greater than an internal diameter of the first outlet end, and an internal diameter of the second inlet end greater than an internal diameter of the second outlet end. In an example, these differences in internal diameter allow the nosepiece to be fitted to additional lumens, while maintaining a substantially constant internal diameter between two connected lumens, such as the first and third lumens of the nasal cannula described below. By maintaining a substantially constant internal diameter through multiple lumens, gas flow through those lumens may be relatively undisturbed, resulting in lower flow resistance and less noise than in typical connections.

The materials used to manufacture the tubing and the system in general may also be selected so as to facilitate smooth flow within the tubing and appropriate durability and connectivity on the outside of the tubing. In some implementations a material of the outer surface comprises at least one of: polyvinyl chloride (PVC) plastic, plastisol, vinyl, silicone, non-latex rubber, an elastomer, ethylene vinyl acetate (EVA), styrene-butadiene copolymer (SBC), polyether ether ketone (PEEK), a polyether block amide (such as PEBAX), a polyethylene material, a high-density polyethylene (HDPE) material, a medium-density polyethylene (MDPE) material, a low-density polyethylene (LDPE) material, a crack-resistant material, a material with a low coefficient of friction, a material less than 70 Durometer Shore A, and flexible plastic. Flexible plastics and the other material examples listed above may be chosen to provide customized comfort to a patient. For example, an infant patient may require a more flexible nosepiece than an adult patient. In such an example, a more flexible material may be chosen.

The cannula is connected to a breathing gas source, and the gas is delivered to the patient through the cannula. In adaptations, a source of breathing gas is connected to the first inlet end and the second inlet end of the respective lumens. The gas flows through the inlet ends and outlet ends of the first and second lumens, then through the nasal prongs to the patient, with each prong inserted into a respective patient nostril during use. In some adaptations high flow therapy (HFT) may be used, which includes delivery of a high flow rate of breathing gas to a patient in through the nosepiece to increase a patient's fraction of inspired oxygen (FiO2) and/or help to facilitate a patient's breathing. In some uses the HFT breathing gas is oxygen; the HFT gas may also be compressed air, and may be humidified air or humidified oxygen.

The bridge may be configured to serve multiple purposes. The bridge may include a first opening, for example along a base of the bridge. The opening increases the flexibility of the bridge. It may further allow medical and/or measurement devices to be coupled to the nosepiece, for example the opening may function as a port for a nebulizer or other drug delivery device. In an example, the bridge is collapsible. The flexibility of a collapsible bridge allows the nosepiece to better conform to irregular facial geometries. A coupling between the nosepiece and a nebulizer would allow nebulized medication to be delivered to a patient together with supplemental breathing gas, allowing a patient to receive the medication without stopping use of a respiratory assist device. A combination of nebulized medication and HFT can be used to assist patients experiencing respiratory distress and provide a comfortable and effective management of cardiopulmonary conditions. The nosepiece allows for delivery of both breathing gas and aerosolized medicament by separate flow paths and separate cannula outlets that are not in fluid communication with each other. The delivery of the aerosolized medicament (attached at the bridge) and breathing gas (delivered by the first and second lumens) by separate tubes allows a source of the aerosolized medicament (e.g., a nebulizer) to be disconnected without interrupting the delivery of the breathing gas.

In another aspect, a nasal cannula is provided for respiratory therapy, comprising a nosepiece and two elongated lumens. The nosepiece is connected to the two elongated lumens. The cannula may be configured to provide breathing gas to a patient by connecting the elongated lumens to a source of breathing gas. The nosepiece may be secured to a user's face, with nasal portions inserted within the patient's nares.

In some implementations, the nosepiece comprises a first lumen, a second lumen, and a bridge. The first lumen has an outer surface. The first lumen comprises a first inlet end to receive a first flow of breathing gas, and a first outlet end to deliver the first flow. The second lumen has an outer surface. The second lumen comprises a second inlet end to receive a second flow of breathing gas, and a second outlet end to deliver the second flow. The bridge separates the first lumen and the second lumen. The bridge may be hollow and have at least one opening. The nosepiece is connected to a third lumen and a fourth lumen. The third lumen of the nasal cannula has an inlet end and an outlet end, and a fourth elongated lumen of the cannula has an inlet end and an outlet end. The nosepiece portion of the nasal cannula is configured to be connected to the outlet ends of the third and fourth lumens. The nasal cannula provides smooth gas paths with a gentler bend than devices in the current state of the art, resulting in low flow resistance, quiet operation, and patient comfort.

The nasal cannula may be implemented by various examples, including those detailed herein. In an example, the first lumen may comprise a first bend between the first inlet end and the first outlet end. The second lumen may comprise a second bend between the second inlet end and the second outlet end. The bridge may attach to the outer surface of the first lumen at the first bend and the outer surface of the second lumen at the second bend. In an example, the bridge may form a fluid barrier between the first lumen and the second lumen. In another example, the bridge may be configured to allow fluid communication between the first flow and the second flow.

In an example, an internal diameter of the first lumen tapers toward the first outlet end, and an internal diameter of the second lumen tapers toward the second outlet end. The output gas flow velocity may be adjusted to suit patient needs by adjusting the internal diameter at the first and second outlet ends. Such a taper increases output gas flow velocity at the first and second outlet ends.

An internal diameter of the first inlet end may be greater than an internal diameter of the first outlet end, and an internal diameter of the second inlet end greater than an internal diameter of the second outlet end. These differences in internal diameter allow the nosepiece to be fitted to additional lumens, while maintaining a substantially constant internal diameter between the lumens. By maintaining a substantially constant internal diameter, gas flow through the lumens may be relatively undisturbed, resulting in lower flow resistance, less rainout, and less noise than in typical connections. In an example, the third lumen and the nosepiece define a constant diameter flow path for the first flow of breathing gas from the inlet end of the third lumen to the outlet end of the first lumen; and the fourth lumen and the nosepiece portion define a constant diameter flow path for the second flow of breathing gas from the inlet end of the fourth lumen to the outlet end of the second lumen. In an example, the first inlet end of the first lumen is adapted to be connected to the outlet end of the third lumen without constricting the internal diameter of the third lumen, and the second inlet end of the second lumen is adapted to be connected to the outlet end of the fourth lumen without constricting the internal diameter of the fourth lumen.

A source of breathing gas may be connected to the inlet ends of the third and fourth lumens. Therefore, the cannula may deliver breathing gas to a patient, through nasal prongs, such as the outlet ends of the first and second lumens, with each prong inserted into a respective nostril during use. HFT may be used to deliver a high flow rate of breathing gas to a patient in through the nasal cannula to increase a patient's fraction of inspired oxygen (FiO2) and/or help to facilitate a patient's breathing A material of the outer surface may comprise at least one of: polyvinyl chloride (PVC) plastic, plastisol, vinyl, silicone, non-latex rubber, an elastomer, ethylene vinyl acetate (EVA), styrene-butadiene copolymer (SBC), polyether ether ketone (PEEK), a polyether block amide (such as PEBAX), a polyethylene material, a high-density polyethylene (HDPE) material, a medium-density polyethylene (MDPE) material, a low-density polyethylene (LDPE) material, a crack-resistant material, a material with a low coefficient of friction, a material less than 70 Durometer Shore A, and a flexible plastic. Flexible plastics and the other material examples listed above may be chosen to provide customized comfort to a patient. For example, an infant patient may require a more flexible nosepiece than an adult patient. In such an example, a more flexible material may be chosen. The third and fourth lumens of the nasal cannula may wrap around a patient's ears and/or around the patient's head. A flexible material may increase the comfort of the patient during use of the nasal cannula.

The bridge may include one or more openings, including, for example, a first opening along a base of the bridge. The opening may increase the flexibility of the bridge. It may further allow medical and/or measurement devices to be coupled to the nosepiece. In an example, the bridge is collapsible. The flexibility of a collapsible bridge allows the nosepiece to better conform to irregular facial geometries.

In an example, the first opening is configured to allow a medical device to be coupled to the nosepiece. In an example, the medical device is a nebulizer. A coupling between the nosepiece and a nebulizer would allow nebulized medication to be delivered to a patient together with supplemental breathing gas, allowing a patient to receive the medication without stopping use of a respiratory assist device. A combination of nebulized medication and HFT can be used to assist patients experiencing respiratory distress and provide a comfortable and effective management of cardiopulmonary conditions. The nosepiece allows for delivery of both breathing gas and aerosolized medicament by separate flow paths and separate cannula outlets that are not in fluid communication with each other. The delivery of the aerosolized medicament (attached at the bridge) and breathing gas (delivered by the first and second lumens) by separate tubes allows a source of the aerosolized medicament (e.g., a nebulizer) to be disconnected without interrupting the delivery of the breathing gas.

In another aspect, a system for respiratory therapy is described. The system comprises a nosepiece portion, a third elongated lumen, a fourth elongated lumen, and a source of breathing gas. The nosepiece portion comprises a first lumen, a second lumen, and a bridge. The first lumen comprises a first inlet end to receive a first flow of breathing gas, a first outlet end to deliver the first flow, and a first bend between the first inlet end and the first outlet end. The second lumen comprises a second inlet end to receive a second flow of breathing gas, a second outlet end to deliver the second flow, and a second bend between the second inlet end and the second outlet end. The bridge, having at least one opening, separates the first lumen and the second lumen. The bridge attaches to the first lumen at the first bend and the second lumen at the second bend. The bridge forms a fluid barrier between the first lumen and the second lumen. The third elongated lumen has an inlet end and an outlet end. The fourth elongated lumen has an inlet end and an outlet end. A source of breathing gas is connected to the inlet ends of the third and fourth lumens. The nosepiece is configured to be connected to the outlet ends of the first and second lumens.

In some implementations, the breathing gas is humidified and heated. Heated and humidified breathing gas may be beneficial for patient respiratory therapy and further increase patient comfort during system use. The nosepiece may be configured according to any of the examples and embodiments referenced herein.

In some implementations, an internal diameter of the first lumen tapers toward the first outlet end, and an internal diameter of the second lumen tapers toward the second outlet end. The output gas flow velocity may be adjusted to suit patient needs by adjusting the internal diameter at the first and second outlet ends. Such a taper increases output gas flow velocity at the first and second outlet ends.

In certain example implementations of the features disclosed herein, the third lumen and the nosepiece define a constant diameter flow path for the first flow of breathing gas from the inlet end of the third lumen to the outlet end of the first lumen; and the fourth lumen and the nosepiece portion define a constant diameter flow path for the second flow of breathing gas from the inlet end of the fourth lumen to the outlet end of the second lumen. In an example, the first inlet end of the first lumen is adapted to be connected to the outlet end of the third lumen without constricting the internal diameter of the third lumen; and the second inlet end of the second lumen is adapted to be connected to the outlet end of the fourth lumen without constricting the internal diameter of the fourth lumen. By maintaining a constant internal diameter, gas flow through the lumens may be relatively undisturbed, resulting in lower flow resistance, less rainout, and less noise than in typical connections.

As noted above, a material of the outer surface may be made of at least one of the following materials: polyvinyl chloride (PVC) plastic, plastisol, vinyl, silicone, non-latex rubber, an elastomer, ethylene vinyl acetate (EVA), styrene-butadiene copolymer (SBC), polyether ether ketone (PEEK), a polyether block amide (such as PEBAX), a polyethylene material, a high-density polyethylene (HDPE) material, a medium-density polyethylene (MDPE) material, a low-density polyethylene (LDPE) material, a crack-resistant material, a material with a low coefficient of friction, a material less than 70 Durometer Shore A, and a flexible plastic. Flexible plastics and the other material examples listed above may be chosen to provide customized comfort to a patient. For example, an infant patient may require a more flexible nosepiece than an adult patient. In such an example, a more flexible material may be chosen.

In an adaptation, the bridge comprises a first opening along a base of the bridge. The opening may increase the flexibility of the bridge. It may further allow medical and/or measurement devices to be coupled to the nosepiece. In an example, the bridge is collapsible. The flexibility of a collapsible bridge allows the nosepiece to better conform to irregular facial geometries.

In an example, the first opening is configured to couple a medical device to the nosepiece. In an example, the medical device is a nebulizer. A coupling between the nosepiece and a nebulizer would allow nebulized medication to be delivered to a patient together with supplemental breathing gas, allowing a patient to receive the medication without stopping use of a respiratory assist device. A combination of nebulized medication and HFT can be used to assist patients experiencing respiratory distress and provide a comfortable and effective management of cardiopulmonary conditions. The nosepiece allows for delivery of both breathing gas and aerosolized medicament by separate flow paths and separate cannula outlets that are not in fluid communication with each other. The delivery of the aerosolized medicament (attached at the bridge) and breathing gas (delivered by the first and second lumens) by separate tubes allows a source of the aerosolized medicament (e.g., a nebulizer) to be disconnected without interrupting the delivery of the breathing gas.

In another aspect, a method for manufacturing a nosepiece for respiratory therapy is described. The method comprises maintaining a plurality of mandrels, and then coating the mandrels with a material. The coated mandrels are cured, and the cured coating is then removed from the mandrels to form a structure made of the coating material.

In some implementations, at least one of the coated mandrels is trimmed before removing the cured coating to create an opening in the coating of the trimmed mandrel. After removing the cured coating, the coating may be further trimmed to achieve the desired structure.

In some implementations, a first, second, and third mandrels are maintained in a fixed arrangement with respect to each other. During the coating step, the third mandrel is positioned between the first and second mandrels and held at a distance from the first and second mandrels. In an example, the coating on the first, second and third mandrels form the first lumen, the second lumen, and the bridge, respectively, of a nosepiece. The three mandrel method of manufacture allows for design freedom and an open geometry of the resulting bridge. The resulting smooth gas paths and flexible bridge lead to lower flow resistance, quieter operation, and increased patient comfort than devices in the current state of the art.

Numerous examples are available for adapting and implementing the method of manufacturing. In an example, the step of coating comprises immersing the fixed arrangement in the material, and removing the arrangement from the material. Dip molding the arrangement provides a relatively economical, in terms of both cost and time, method of manufacture of the above-described nosepiece, while allowing for nosepiece customization. In an example, the step of coating comprises spraying the material onto the arrangement. In an example, the first, second, and third mandrels are fixedly held on a substrate. This may keep the mandrels in the desired arrangement for the step of coating.

In another aspect, a method for respiratory therapy is described. The method comprises receiving two separate flows of breathing gas through two inlet ends of a nosepiece and delivering the two flows through two respective outlet ends. The first flow of breathing gas is received at a first inlet end of a first lumen. The second flow of breathing gas is received at a second inlet end of a second lumen. The first flow is delivered through a first outlet end of the first lumen, while the second flow is delivered through a second outlet end of the second lumen.

In some implementations and as described above, the first lumen and second lumen may be part of a nosepiece. The nosepiece may further comprise a bridge separating the first lumen and the second lumen. The bridge may have at least one opening. In some instances, the bridge may be configured to maintain the first flow separate from the second flow. In some instances, the bridge maybe configured to allow the first flow and the second flow to be in fluid communication. For instance, the bridge may be configured with small flow channels or membranes that permit flow, osmosis, or any other suitable fluid communication between the lumens and the bridge.

In some implementations, a flow feedback loop, an inherent flow limitation, a pressure feedback loop, a balancing shunt, or any other suitable system may be implemented to increase patient comfort if an occlusion occurs in the first lumen or the second lumen.

In an example, the first lumen has a first bend and the second lumen has a second bend. The bridge may connect to the outer surface of the first lumen at the first bend and the outer surface of the second lumen at the second bend.

In an example, the first flow and the second flow are heated and humidified. Heated and humidified breathing gas may be beneficial for patient respiratory therapy and further increase patient comfort during system use. The nosepiece may be configured according to any of the examples and embodiments referenced herein.

Variations and modifications will occur to those of skill in the art after reviewing this disclosure. The disclosed features may be implemented, in any combination and subcombination (including multiple dependent combinations and subcombinations), with one or more other features described herein. The various features described or illustrated above, including any components thereof, may be combined or integrated in other systems. Moreover, certain features may be omitted or not implemented.

BRIEF DESCRIPTION OF THE DRAWINGS

The foregoing and other objects and advantages will be apparent upon consideration of the following detailed description, taken in conjunction with the accompanying drawings, in which like reference characters refer to like parts throughout, and in which.

DETAILED DESCRIPTION

To provide an overall understanding of the systems, methods, and devices described herein, certain illustrative implementations will be described. Although the implementations and features described herein are specifically described for use in connection with a high flow therapy system, it will be understood that all the components and other features outlined below may be combined with one another in any suitable manner and may be adapted and applied to other types of respiratory therapy and respiratory therapy devices, including low flow oxygen therapy, continuous positive airway pressure therapy (CPAP), mechanical ventilation, oxygen masks, Venturi masks, and Tracheostomy masks. Furthermore, it should be noted that while certain implementations are discussed herein within regards to manufacturing nosepieces and systems for respiratory therapy, these various implementations may be used in various combinations to increase both the efficacy of treatment and the patient's overall level of comfort during the treatment.

Disclosed herein are systems, methods, and devices providing a bifurcated nasal cannula with low flow resistance and increased patient comfort. A nosepiece for respiratory therapy is described below that provides a custom bridge between nasal prongs of a nasal cannula with a smooth bore gas path. The nosepiece may be manufactured by dip molding at least three mandrels fixedly arranged relative to each other. The three mandrel method allows for design freedom and an open geometry of the nasal bridge. Sacrificial material may be molded completely around the third mandrel and then trimmed. The relatively low monetary cost of the dip molding material allows for discarding the excess material without significantly affecting the production cost.

The methods described for creating a dip molded bifurcated cannula that has low gas flow resistance also create nasal bridges that are flexible and can conform to irregular facial geometries. The systems, methods, and devices described herein provide a smooth gas path with a gentler bend than devices in the current state of the art, resulting in low flow resistance, quiet operation, and patient comfort. The low flow resistance of the disclosed devices is especially important for devices that provide the flow of gas through nasal cannulas by means other than compressed gas provided by a hospital. For example, the low flow resistance of the disclosed devices may be beneficial in home use respiratory therapy systems. The smooth bore design of the systems, method, and devices described herein eliminates places for moisture to coalesce and therefore reduces rainout.

Figure 1:
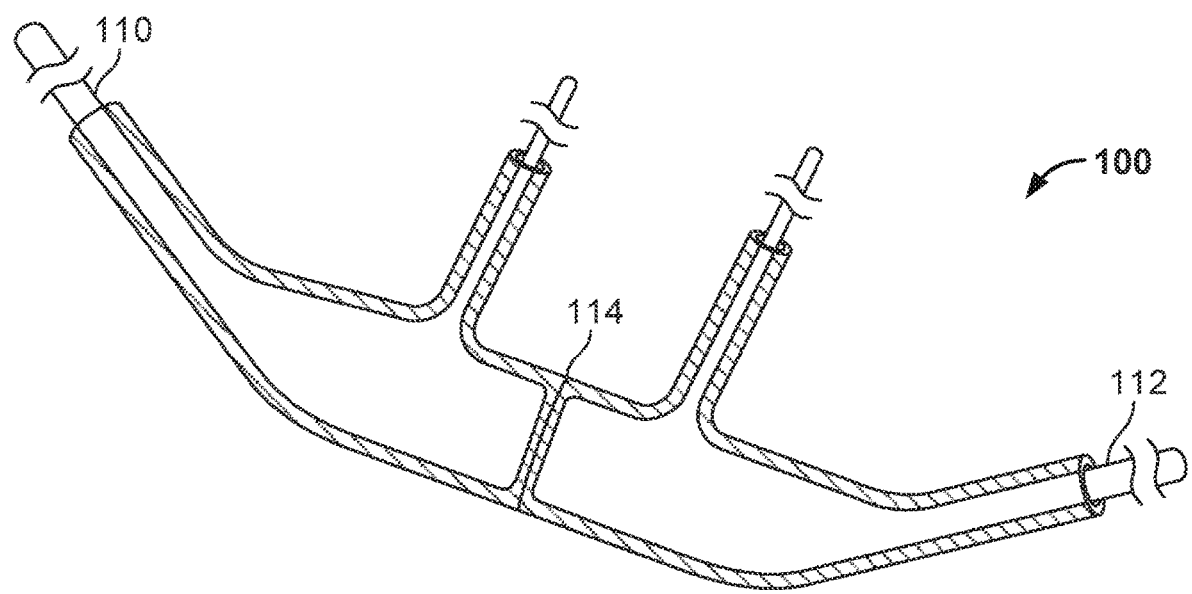
FIG. 1 shows an illustrative prior art nasal cannula nosepiece mandrel arrangement.

FIG. 1 shows an illustrative prior art nasal cannula nosepiece mandrel arrangement. A first mandrel 110 is placed in close proximity to a second mandrel 112. A small gap 114 is left between the two mandrels 110 and 112. Mandrels 110 and 112 may be dipped in liquid material to create a dip mold. Liquid plastic may flow into gap 114 that connects mandrels 110 and 112, sealing off the gas path between the two halves of the nosepiece and forming a ridge (as shown in FIG. 2 and described below).

Figure 2:
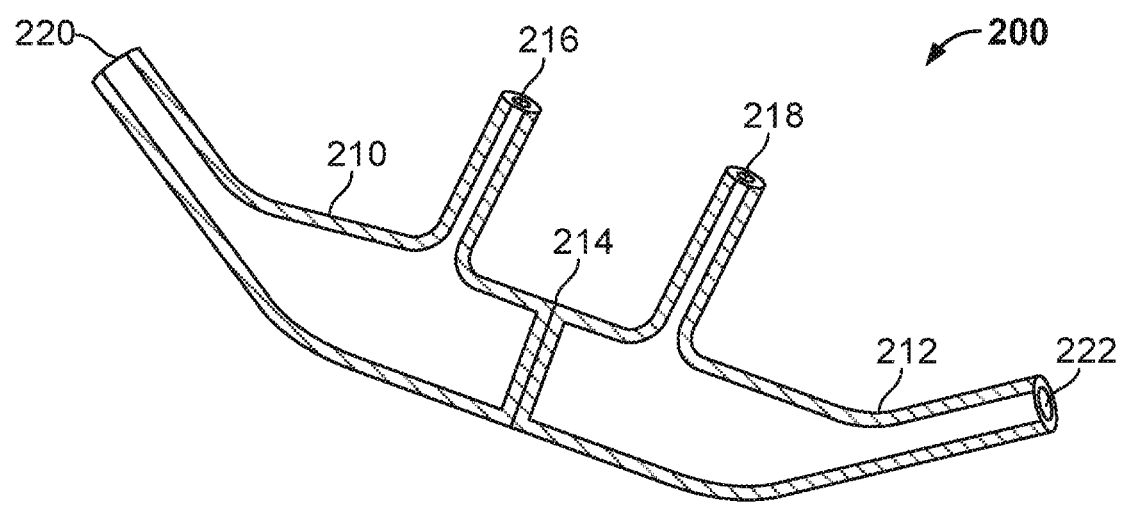
FIG. 2 shows an illustrative prior art nasal cannula nosepiece.

FIG. 2 shows an illustrative prior art nasal cannula nosepiece 200. Nosepiece 200 may be made using the mandrel arrangement of FIG. 1. A first section 210 and a second section 212 of the nosepiece are separated by ridge 214. Outputs 216, 218 may output breathing gas to a patient. Breathing gas may be input to parts 220 and 222. Sections 212 and 210 are configured to have relatively wide diameters (compared to the diameters of input parts 222 and 220) where they join at ridge 214. This provides a surface for the nosepiece to rest beneath the patient's nose. However, the orientation of connecting ridge 214 creates a hard feeling piece of plastic where it contacts the skin on the upper lip, which can cause patient discomfort. Furthermore, the geometry of nosepiece 200 and, in particular, placement of ridge 214, creates an inflexible surface where the nosepiece rests on the patient's face, which can cause the nosepiece to roll outward, away from the patient's face, and additionally increases the amount of discomfort the patient feels.

The wide diameter of sections 210 and 212, combined with the sharp change in direction of breathing flow at ridge 214, causes a high flow resistance gas path and disruptions in the flow of breathing gas. Consequences of the disruptions can be loss of heat from the breathing gas, liquid formation and excess water dripping (rainout), and pressure drop, which can decrease the efficacy of respiratory therapy. The shape of the sections 210 and 212 also can create a high level of noise during operation, which can further increase patient discomfort.

Systems, methods, and devices providing a bifurcated nasal cannula with low flow resistance and increased patient comfort are disclosed herein to remedy the deficiencies of the prior art shown in FIGS. 1 and 2 and described above. For example, a nosepiece for respiratory therapy is described below that provides a custom bridge between nasal prongs of a nasal cannula with a smooth bore gas path. The nosepiece may be manufactured by dip molding three mandrels fixedly arranged around each other. The three mandrel method allows for design freedom and an open geometry of the nasal bridge.

Figure 3:
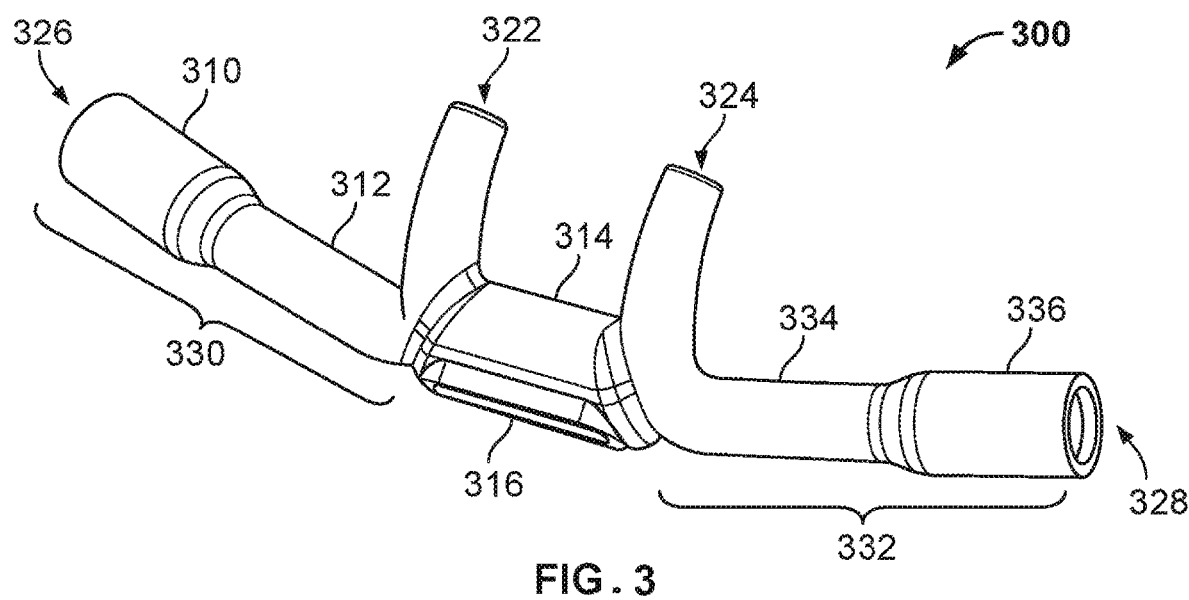
FIG. 3 shows an illustrative nosepiece of a nasal cannula for respiratory therapy.

FIG. 3 shows an illustrative nosepiece 300 of a nasal cannula for respiratory therapy. Nosepiece 300 comprises a first lumen 330, a second lumen 332, and a bridge 314.

Nosepiece 300 may desirably be shaped to prevent sharp changes in direction of the flow of breathing gas within lumens 330 and 332. Lumens 330 and 332 may be, for example, nasal prongs used to deliver breathing gas to nares of a patient. First lumen 330 has an outer surface 310, 312. Outer surface 310, 312 may form a tube. First lumen 330 has a first inlet end 326 to receive a first flow of breathing gas, a first outlet end 322 to deliver the first flow, and a first bend between first inlet end 326 and first outlet end 322. Second lumen 332 has an outer surface 334, 336. Outer surface 334, 336 may also form a tube. Second lumen 332 has a second inlet end 328 to receive a second flow of breathing gas, a second outlet end 324 to deliver the second flow, and a second bend between second inlet end 328 and second outlet end 324.

In certain implementations, nosepiece 300 is formed from a flexible material (e.g., polyvinyl chloride (PVC) plastic, plastisol, vinyl, silicone, non-latex rubber, an elastomer, ethylene vinyl acetate (EVA), styrene-butadiene copolymer (SBC), polyether ether ketone (PEEK), a polyether block amide (such as PEBAX), a polyethylene material, a high-density polyethylene (HDPE) material, a medium-density polyethylene (MDPE) material, a low-density polyethylene (LDPE) material, a crack-resistant material, a material with a low coefficient of friction, a material less than 70 Durometer Shore A, or any other flexible plastic).

Bridge 314 spatially separates first lumen 330 and second lumen 332. Bridge 314 attaches to the outer surface 310, 312 of first lumen 330 at the first bend and attaches to the outer surface 334, 336 of second lumen 332 at the second bend. Bridge 314 has at least one opening 316 and is hollow. Bridge 314 may fluidically seal the two lumens 330 and 332 from each other, and maintain the first flow of breathing gas in the first lumen 330 separate from the second flow of breathing gas in the second lumen 332. For example, the bend in sections 334 and the bend in section 312 may attach to bridge 314, while maintaining a solid barrier between lumens 330 and 332 and bridge 314. Preventing the first and second flows of breathing gas from mingling helps to prevent disruptions to the breathing gas flow delivered to a patient, which in turn reduces rainout and the coalescence of large droplets of rainout. Rainout may be uncomfortable and potentially dangerous to patients. The separation of lumens 330 and 332 also allows for a smooth bore gas path, providing a steady flow of breathing gas to a patient.

Bridge 314 may act as a "pillow" to provide a comfortable fit for patients using the nosepiece and prevent nosepiece 300 from rolling outward from a patient's nose. Bridge 314 may be customized to provide different levels of flexibility and greater comfort to patients, especially those with unique facial features. For example, bridge 314 may be three-sided, cylindrical, four-sided, etc., depending on patient needs. Bridge 314 may be hollow to allow greater flexibility and lighter weight. Opening 316 is along a base of bridge 314. Opening 316 may be a variety of shapes, allowing for the bridge to collapse more easily and conform to patients' unique facial geometry.

Figure 10:
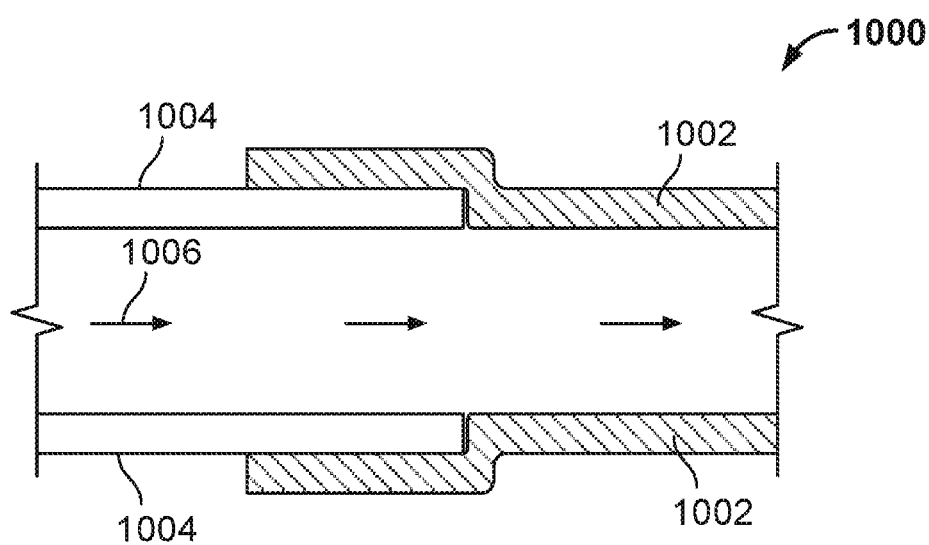
FIG. 10 shows an illustrative connection to maintain a constant inner diameter between two lumens.

First lumen 330 comprises a first section 310 and a second section 312. The internal diameter of sections 310 and 312 may be different. Second lumen 332 comprises a first section 334 and a second section 336. The internal diameter of sections 334 and 336 may be different. The difference in internal diameter between sections 310 and 312, and 334 and 336 allows for different diameters for inlet ends 326, 328 and outlet ends 322, 324. For example, as shown in FIG. 3, an internal diameter of the first inlet end 326 is greater than an internal diameter of the first outlet end 322, and an internal diameter of the second inlet end 328 is greater than an internal diameter of the second outlet end 324. In certain implementations, the nosepiece shown in FIG. 3 may be part of nasal cannula comprising third and fourth elongated lumens (shown in FIG. 8). The change in internal diameter between sections 310 and 312, sections 334 and 336 may allow the third and fourth elongated lumens to be fitted within sections 310, 336 respectively, as shown in FIG. 10 and described below. By fitting a lumen, for example through a solvent bonded connection, the same constant internal diameter may be maintained through the third and fourth lumens into sections 312 and 334, respectively.

The diameter of sections 312 and 334 may taper to outlet ends 322 and 324, respectively. A taper may begin where section 310 meets section 312 or before or after the bend in section 312. A taper may begin where section 334 meets section 336 or before or after the bend in section 334. The diameter of ends 322 and 324 will affect output gas flow velocity from nosepiece 300. For example, the diameter of section 312 may decrease as section 312 approaches outlet end 322. Such a decrease in diameter increases output gas flow velocity at outlet end 322. Output gas flow velocity may therefore be adjusted to suit patient needs by adjusting the diameter at outlet ends 322 and 324. However, as gas flow approaches outlet end 322 or 324, a narrowing taper may increase flow resistance. Increasing the abruptness of the taper increases the flow resistance for gas flows through sections 330 and 332. To decrease flow resistance, the taper may be gradual.

Figure 8:
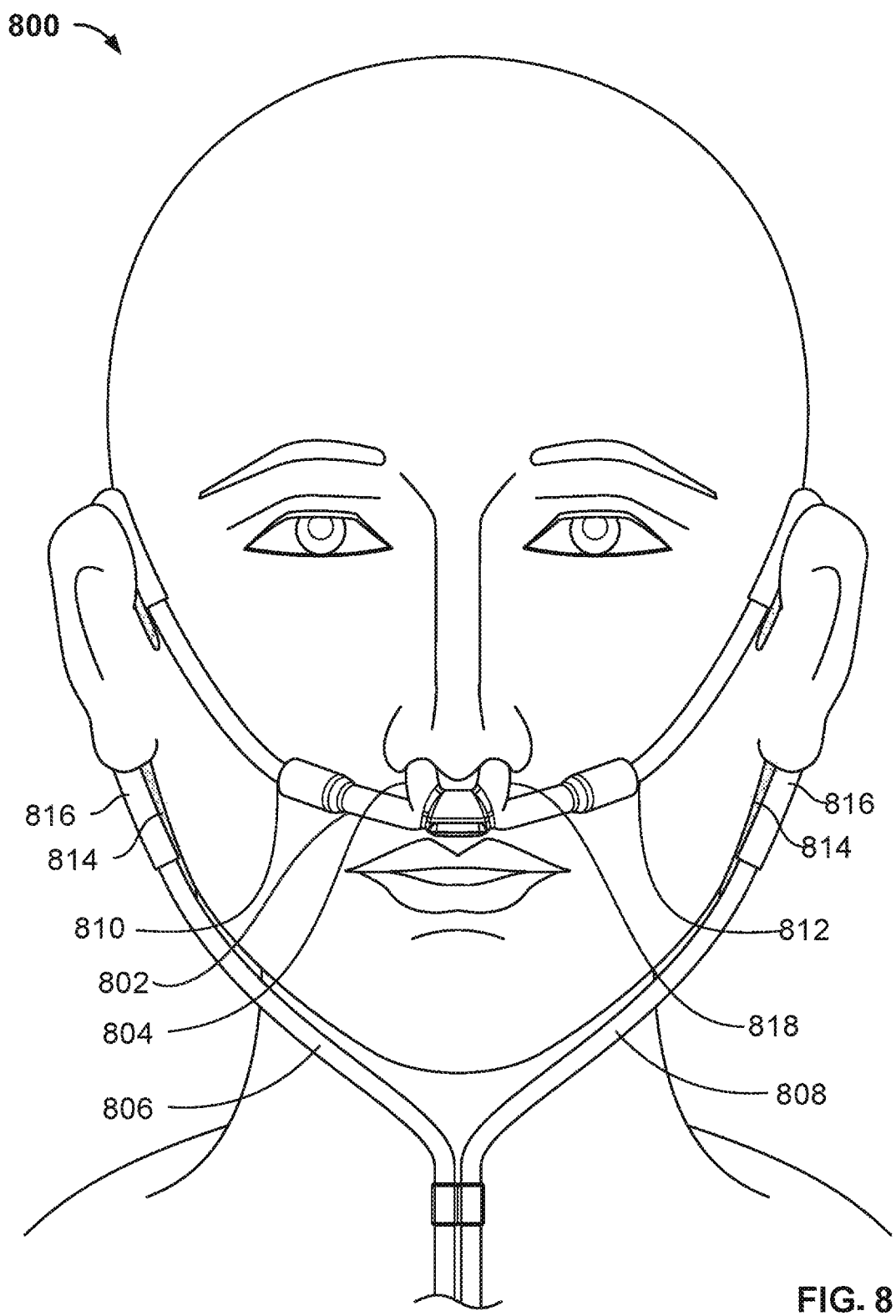
FIG. 8 shows an illustrative nasal cannula.

Nosepiece 300 is not limited to the above components, but may include alternative or additional components, as would be understood by one of ordinary skill in the art from the description herein. For example, nosepiece 300 may be connected to additional lumens as shown in FIG. 8 and described below. Nosepiece 300 may be part of system for respiratory therapy, such as HFT, and may be connected to a gas source, nebulizer, and/or nasal cannula for delivery of heated and humidified air with or without aerosolized medicament.

In some implementations, opening 316 may be configured to allow a medical device to be coupled to nosepiece 300. For example, opening 316 may be used to connect a medical device tube to nosepiece 300. In some implementations, bridge 314 may have more than one opening. For example, bridge 314 may have an opening along its base and its top, allowing a tube to be threaded through bridge 314 and held in place by an attachment or friction fitting. In some implementations, a device to measure a patient's breathing rate may be coupled to nosepiece 300.

Such couplings between medical devices and nosepiece 300 may be accomplished through fittings wherein the medical device "snaps" into opening 316. For example, a ball-like connector of the medical device or nebulizer may sit in the cavity of bridge 314, forming a lock-type fit between the device and nosepiece 300, or forming a ball and socket joint.

In some implementations, a nebulizer may be coupled to nosepiece 300 at opening 316. Nebulizers allow aerosolized respiratory medications, such as bronchodilators (e.g., Albuterol (Ventolin), Salbutamol (Proventil), Levosalbutamol/Levalbuterol (Xopenex)) for treating asthma or Chronic Obstructive Pulmonary Disease (COPD) to be administered through inhalation directly to a patient's lungs. Such a coupling between nosepiece 300 and a nebulizer would allow nebulized medication to be delivered to a patient together with supplemental breathing gas (as provided via lumens 330, 332), allowing a patient to receive the medication without stopping use of a respiratory assist device. For example, the aerosolized medication may be delivered through a separate third outlet end of the nebulizer. During respiratory therapy, the breathing gas and aerosolized medicament may merge through the slipstream effect. A combination of nebulized medication and HFT can be used to assist patients experiencing respiratory distress and provide a comfortable and effective management of cardiopulmonary conditions.

Nosepiece 300 allows for delivery of both breathing gas and aerosolized medicament by separate flow paths and separate cannula outlets that are not in fluid communication with each other. The delivery of the aerosolized medicament (attached at bridge 314) and breathing gas (delivered by lumens 330 and 332) by separate tubes allows a source of the aerosolized medicament (e.g., a nebulizer) to be disconnected without interrupting the delivery of the breathing gas. Unlike systems that use a 'T' or 'Y' adaptor to connect a nebulizer to a respiratory therapy circuit, the nosepiece 300 involves no junction point between the flow of aerosolized medicament and the flow of breathing gas. Thus, removal of the source of aerosolized medicament does not introduce another opening in the breathing gas circuit, and the source of aerosolized medicament can be simply removed without having to place a plug or cap in its place. Similarly, a device to measure the breathing rate of a patient may be attached or detached to nosepiece 300 with minimal disruption to the patient.

In some instances, bridge 314 may be configured to allow the first flow of breathing gas through lumen 330 and the second flow of breathing gas through lumen 332 to be in fluid communication with each other. For instance, bridge 314 may be configured with small flow channels or membranes that permit flow, osmosis, or any other suitable fluid communication between lumens 330, 332 and bridge 314. Specifically, bridge 314 may comprise a plurality of openings, in addition to opening 316, configured to allow medicament to flow from an attached medicament delivery device, such as a nebulizer, to lumens 330 and 332. These openings may allow aerosolized medicament from the attached medicament delivery device to join the first and second breathing gas flows through a slipstream effect, as described in U.S. Pat. No. 9,333,317, the contents of which is hereby incorporated by reference in its entirety.

Nosepiece 300 may be part of a system for respiratory therapy with a source of heated and humidified breathing gas. Heating and humidifying breathing gas may increase patient comfort. For example, providing heated and humidified breathing gas to the patient along with aerosol from a nebulizer can increase patient comfort by counterbalancing the cooling and drying sensations associated with the delivery of aerosol to the nostril.

Nosepiece 300 may be used in a method for respiratory therapy. Such a method may comprise receiving two separate flows of breathing gas through the two inlet ends 328, 326 of nosepiece 300 and delivering the two flows through two respective outlet ends 322, 324. The first flow of breathing gas through section 312 and the second flow of breathing gas through section 334 may be heated and humidified.

Figure 4:
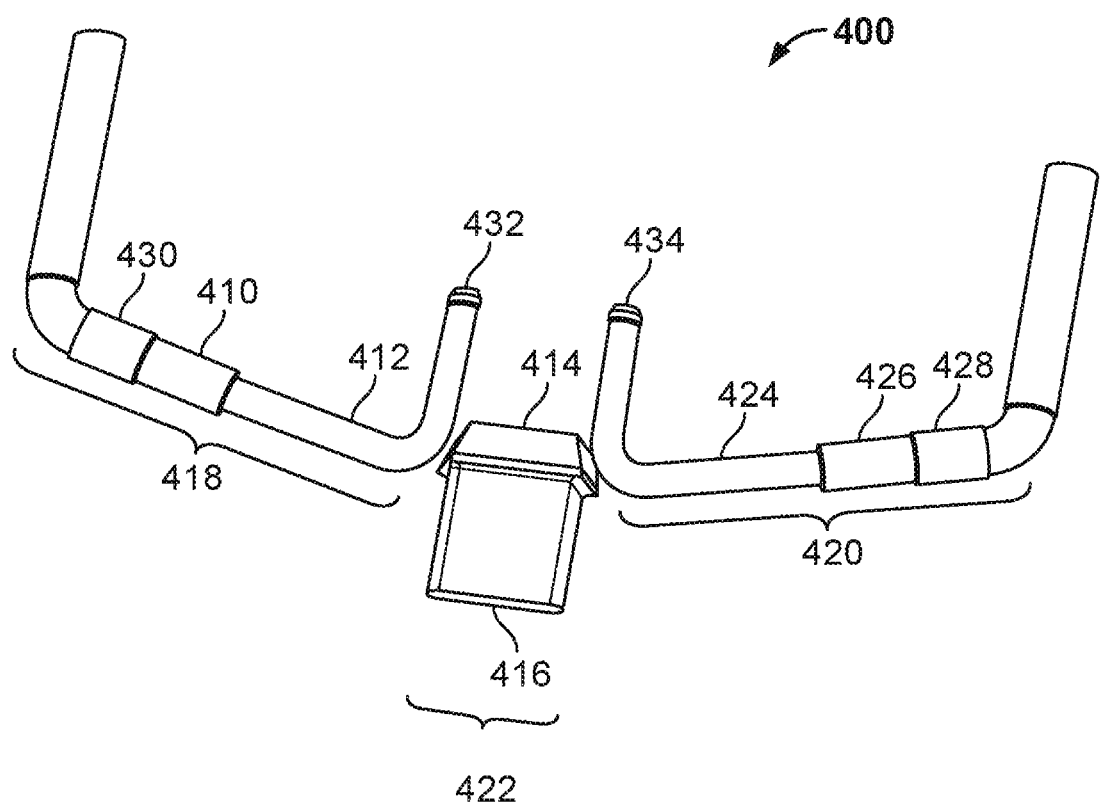
FIG. 4 shows an illustrative mandrel arrangement for manufacturing a nosepiece of a nasal cannula for respiratory therapy.

FIG. 4 shows an illustrative mandrel arrangement 400 for manufacturing a nosepiece of a nasal cannula for respiratory therapy. For example, mandrel arrangement 400 may be used to manufacture nosepiece 300, as shown in FIG. 3. Arrangement 400 comprises a first mandrel 418, a second mandrel 420, and a third mandrel 422. Third mandrel 422 is placed in close proximity between first mandrel 418 and second mandrel 420.

The first mandrel 418 has a circular cross section and comprises two diameters: a first diameter through section 410 and a second diameter through section 412. The diameter of section 412 is less than the diameter of section 410. The second mandrel 420 has a circular cross section and comprises two diameters: a first diameter through section 426 and a second diameter through section 424. The diameter of section 424 is less than the diameter of section 426. In certain implementations, the diameter of section 410 may be the same as the diameter of section 426. In certain implementations, the diameter of section 412 may be the same as the diameter of section 424. In certain implementations, the first mandrel 418 may further comprise a third diameter through section 430. The third diameter through section 430 may be the same as or different than the first diameter through section 410. In certain implementations, the second mandrel 420 may further comprise a third diameter through section 428. The third diameter through section 428 may be the same as or different than the first diameter through section 426.

The diameter of sections 412 and 424 may taper to ends 432 and 434, respectively. A taper may begin where section 410 meets section 412 or before or after the bend in section 412. A taper may begin where section 426 meets section 424 or before or after the bend in section 424. The diameter of ends 432 and 434 will affect output gas flow velocity from the nosepiece formed by mandrels 418, 420, and 422. For example, the diameter of section 412 may decrease as section 412 approaches end 432. Such a decrease in diameter increases output gas flow velocity at the output of a nosepiece formed on mandrel 418 (such as the output from outlet end 322 of FIG. 1). The diameter at outlet ends 322 and 324 may be adjusted to suit patient needs.

The third mandrel 422 comprises an upper portion 414 and a lower portion 416. The distal end of portion 414 is attached to the proximal end of portion 416. The distal end of portion 414 is larger than the proximal end of portion 416 so as to create an undercut. Portion 414 is placed between section 412 and section 424 of first mandrel 418 and second mandrel 420, respectively.

Mandrels 418, 420, 422 are in a fixed arrangement with respect to each other. Third mandrel 422 is arranged between first mandrel 418 and second mandrel 420. Section 414 of third mandrel 422 is placed between a bend in section 412 and a bend in section 424. A small distance is left between section 414 and sections 412 and 424, respectively. For example, the distance may be 3 mm, 2 mm, 1 mm, or any other suitable distance.

In some implementations, the arrangement is coated with a material. For example, the material may be, polyvinyl chloride (PVC) plastic, plastisol, vinyl, silicone, non-latex rubber, an elastomer, a material less than 70 Durometer Shore A, ethylene vinyl acetate (EVA), styrene-butadiene copolymer (SBC), polyether ether ketone (PEEK), a polyether block amide (such as PEBAX), a polyethylene material, a high-density polyethylene (HDPE) material, a medium-density polyethylene (MDPE) material, a low-density polyethylene (LDPE) material, a crack-resistant material, a material with a low coefficient of friction, flexible plastic, or any other suitable material.

The distance between mandrels 418, 420, and 422 allows material to flow around the mandrels and form two lumens and a hollow bridge, while sealing off the gas path between the two lumens. The arrangement may be coated by, for example, fixedly holding mandrels 418, 420, and 422 on a substrate and dipping arrangement 400 in liquid material, spraying material onto arrangement 400, dipping arrangement 400 arranged on a rack into material, or any other suitable means.

After arrangement 400 is coated in material, it may be cured. For example, the coated arrangement may be cured at room temperature, or at a temperature or set of temperature (such as those determined by the material's curing temperature profile) determined to accelerate the curing time. For example, the coating may be cured using a heat lamp, oven, UV radiation or any other suitable means. After curing, at least one coated mandrel may be trimmed to create an opening in the coating of the trimmed mandrel. For example, mandrel 422 may be a "sacrificial" mandrel. Coated mandrel 422 may be trimmed to allow the pertinent cured coating to be removed from mandrel 422. The cured coating on mandrel 422 may correspond to bridge 314 of FIG. 3. Trimming the coating allows for the different openings of bridge 314, as described above. The cured coating may then be removed from arrangement 400 to leave a single intact structure. For example, the cured coating may be a flexible plastic that is in the shape of the nosepiece shown FIG. 3. For example, mandrels 418 and 420 may form lumens 330 and 332, respectively, while mandrel 422 may form hollow bridge 314. The material coating is joined where there was distance left between mandrels 418, 420, and 420. By leaving a small distance between the mandrels, the material that flows around the mandrels will separate the structures formed by the mandrels with a thin layer of material.

Mandrel 422 geometry may be of any shape such that it comes within close proximity of mandrels 418 and 420 that form the gas path of the nosepiece. The bridge created by mandrel 422 and connecting the coatings on mandrels 418 and 422 can be three-sided or hollow, allowing for the bridge to collapse more or less easily and, therefore, better conform to patients' unique facial geometry. The inherent opening of the coating of mandrel 422 can also be any shape, so long as mandrel 422 can be forcibly pulled through the flexible opening of material coating it. Varying the opening of the bridge formed by mandrel 422 can be done to perform different functions, such as adding intentional undercuts or to aid in the collapsibility of the bridge. Mandrel 422 may include raised patterns or ribbing to alter the inner surface of the coating on mandrel 422. These alterations to the inner surface of the coating may add strength and/or alter the flexibility of bridge 314 of FIG. 3.

This method allows for the design of nearly any bridge geometry to provide customized comfort and ergonomics to patients. The form of the bridge is no longer tied to the round or rectangular geometries required by manufacture. Dip molding, for example, allows for smaller production runs, more effective cost, less time, and more customizable geometries than traditional manufacturing means.

Figure 5:
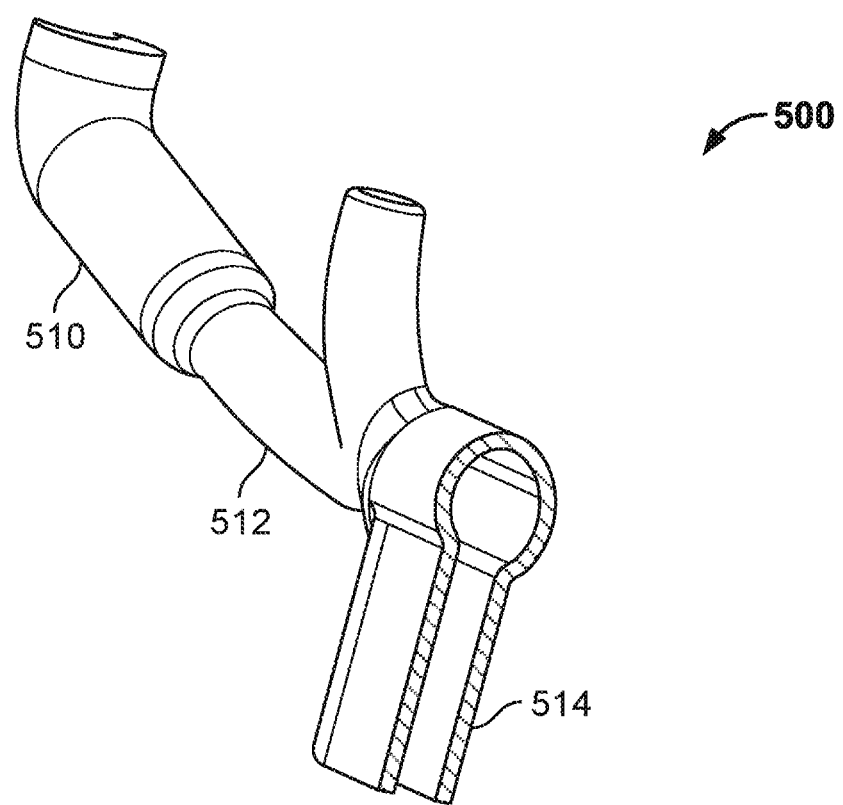
FIG. 5 shows an illustrative cross-sectional view of a bridge of a nosepiece before trimming excess plastic away.

FIG. 5 shows an illustrative cross-sectional view 500 of a bridge of a nosepiece before trimming excess material away. For example, FIG. 5 may represent a portion of a structure similar to that of FIG. 3, wherein section 510 corresponds to section 310 and section 312 corresponds to section 312 of lumen 330. After the mandrel arrangement of FIG. 4 is coated with material and cured, the coated, cured material must be removed from the arrangement. The mandrel forming the bridge (such as mandrel 422 of FIG. 4) may be entirely coated in cured material. The bridge mandrel itself is a "sacrificial" mandrel and may be trimmed to provide an opening for the bridge mandrel to be removed through. The sacrificial material is molded completely around the third mandrel that must be cut off. The relatively low cost of the material allows for discarding the excess.

After the sacrificial mandrel is removed, opening 514 remains. Opening 514 may then be trimmed to suit the needs of a patient. For example, the opening may be trimmed close to the connection with lumen 512 (as shown in FIG. 3 at opening 316). In another instance, the opening may not be trimmed as closely, and may instead leave the majority of opening 514 to provide an input "tube" to attach a medical device. Other openings may further be trimmed in the structure of opening 514, such as creating a second opening to allow a medical device to be threaded through the nasal bridge. The trimming may depend on the patient's facial structure, the amount of flexibility needed, the configuration of devices to attach to the bridge, or other suitable factors.

Figure 6:
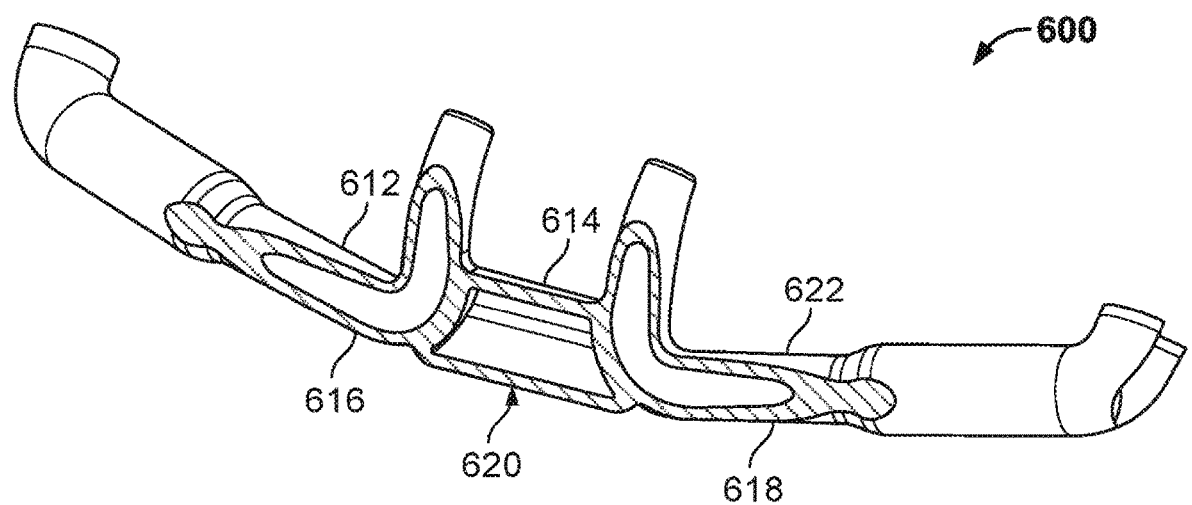
FIG. 6 shows an illustrative cross-sectional view of a nosepiece formed by three mandrels located in close proximity.

FIG. 6 shows an illustrative cross-sectional view 600 of a nosepiece formed by three mandrels located in close proximity to form connecting ribs, after the sacrificial mandrel has been trimmed. For example, FIG. 6 may represent a structure similar to that of FIG. 3, wherein section 612 corresponds to section 312, section 622 corresponds to section 334, and section 614 corresponds to section 314. As shown by cross section 616, section 612 forms a lumen with a smooth inner surface. As shown by cross section 618, section 622 forms a lumen with a smooth inner surface similar to that of section 612. As shown by cross section 620, section 614 is a hollow bridge between sections 612 and 622. The hollow space surrounded by section 614 is isolated from the lumens formed by sections 612 and 622. As such, breathing gas flowing through the lumen formed by section 612 is separated from breathing gas flowing through the lumen formed by section 622. No breathing gas enters section 614. The separation between sections 612 and 622 may help to decrease disruptions to gas flow during delivery to patients.

Figure 7:
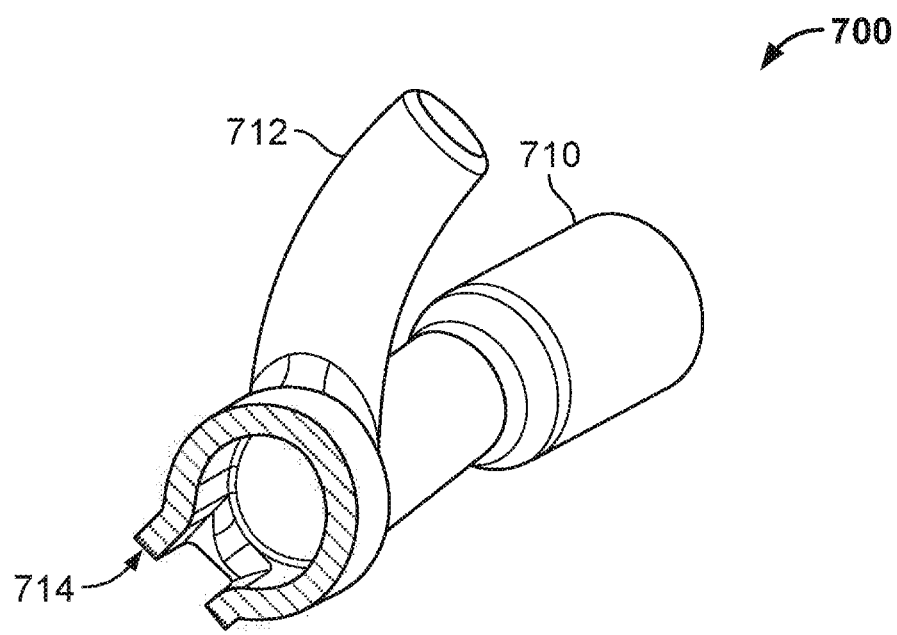
FIG. 7 shows an illustrative cross-sectional view of a bridge of a nosepiece.

FIG. 7 shows an illustrative cross-sectional view of a bridge of a nosepiece. Section 710 corresponds to section 310 of FIG. 3, and section 712 corresponds to section 312 of FIG. 3. Section 714 illustrates a cross section of bridge 314 of FIG. 3 after excess material is trimmed away and the mandrels have been removed. Section 712 is a nasal prong used to deliver breathing gas to the nostril of a patient. Inlet section 710 may connect to a separate lumen to, for instance, form a nasal cannula. Breathing gas may flow in through inlet section 710 through section 712 to the patient. While section 714 is connected to section 712, breathing gas does not flow through section 714, because there is a thin barrier of flexible material between the two sections. This barrier prevents breathing gas from escaping section 712 before reaching its outlet end and the nostril of the patient and is a result of the dip molding process with the three mandrels discussed above in relation to FIG. 4.

FIG. 8 shows an illustrative nasal cannula in use by a patient. Nasal cannula 800 comprises a nosepiece portion 802, a third lumen 806, and a fourth lumen 808. Nosepiece portion 802 corresponds to nosepiece 300 as shown in FIG. 3 and described above. The third elongated lumen 806 has an inlet end and an outlet end. Fourth elongated lumen 808 has an inlet end and an outlet end. Nosepiece portion 802 is connected to the outlet end of third lumen 806 at connection 810 and the outlet end of fourth lumen 808 at connection 812. Nasal cannula 800 may include, for example, padding 814 and 816 around the patient's ears for added comfort.

The third lumen 806 and nosepiece portion 802 define a constant diameter flow path for the first flow of breathing gas from the inlet end of the third lumen to the outlet end 804 of the first lumen (lumen 330 of FIG. 3). Fourth lumen 808 and the nosepiece portion 802 define a constant diameter flow path for the second flow of breathing gas from the inlet end of fourth lumen 808 to the outlet end 818 of the second lumen (lumen 332 of FIG. 3). The constant internal diameter of the flow paths decreases noise creation during breathing gas delivery by preventing disruptions (e.g. eddies) in breathing gas flow. Minimizing noise during cannula use may increase a patient's comfort level.

In certain implementations, the first inlet end of the first lumen is adapted to be connected to the outlet end of third lumen 806 without constricting the internal diameter of third lumen 806. The second inlet end of the second lumen is adapted to be connected to the outlet end of fourth lumen 808 without constricting the internal diameter of fourth lumen 808. For example, the connections between third lumen 806, fourth lumen 808, and nosepiece 802 may be similar to the connection shown in FIG. 9 and described below.

Nasal cannula 800 is not limited to the above components, but may include alternative or additional components, as would be understood by one of ordinary skill in the art from the description herein. For example, nasal cannula 800 may be part of a system for respiratory therapy. The system may comprise the nosepiece described above and a source of breathing gas. In an exemplary implementation, the source generates heated and humidified breathing gas for delivery to the patient. The source may be configured to provide, for example, breathing gas at flow rates between 1 and 8 liters per minute (lpm) for infants, between 5 and 20 lpm for pediatric patients, or up to 40 lpm for adults. Suitable sources of heated and humidified gas will be known to one of ordinary skill in the art. For example, the source may be the Vapotherm Flowrest System, Vapotherm Careflow System, Precision Flow unit, or the Vapotherm 2000*i*, all of which are provided by Vapotherm, Inc. of Exeter, New Hampshire, USA. Other suitable sources of breathing gas will be known to one of ordinary skill in the art from the description herein.

Figure 9:
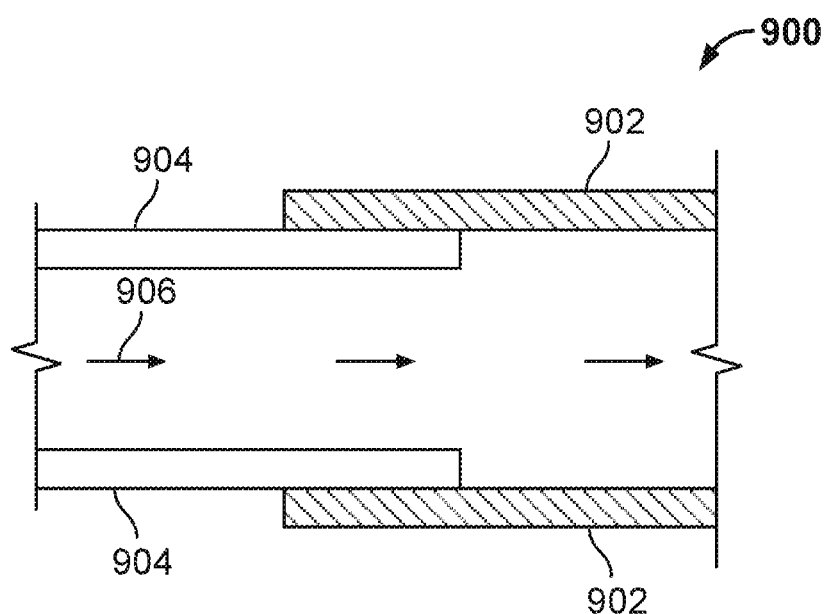
FIG. 9 shows a non-desirable but typical to prior art connection between two lumens.

FIG. 9 shows a non-desirable but typical to prior art connection between two lumens. A first lumen is defined by tube 902. A second lumen is defined by tube 904. Tube 904 has a smaller internal diameter than tube 902. Tube 904 fits into 902, creating an airtight seal through, for example, a friction fitting. Breathing gas flow 906 flows through tube 904 to tube 902. The sharp change in internal diameter between tubes 904 and 902 creates eddies and disruptions in gas flow 906. Such disruptions cause, for example, noise and resistance in the gas flow path, making the connection less efficient and any system using such connection for a nasal cannula less comfortable for a patient. In some implementations, there may be a coupling to connect tubes 904 and 902.

FIG. 10 shows an illustrative connection to maintain a constant inner diameter between two lumens. A first lumen is defined by tube 1002. A second lumen is defined by tube 1004. Tube 1002 is connected to tube 1004 without constricting the internal diameter of tube 1004. Tube 1002 has an enlarged portion 1008. Enlarged portion 1008 has an internal diameter equal to the outer diameter of tube 1004. Tube 1002 transitions to the internal diameter of tube 1004, thereby maintaining a substantially constant diameter between tubes 1002 and 1004. Breathing gas flow 1006 flows through tube 1004 to tube 1002. By maintaining a constant inner diameter, gas flow 1006 may be relatively undisturbed resulting in lower flow resistance and less noise than the typical connection shown in FIG. 9. Such a connection may be used, for example, to connect the nosepiece of FIG. 3 to elongated lumens to form a nasal cannula or system for respiratory therapy, as described above. This connection may be a solvent bonded connection.

Figure 11:
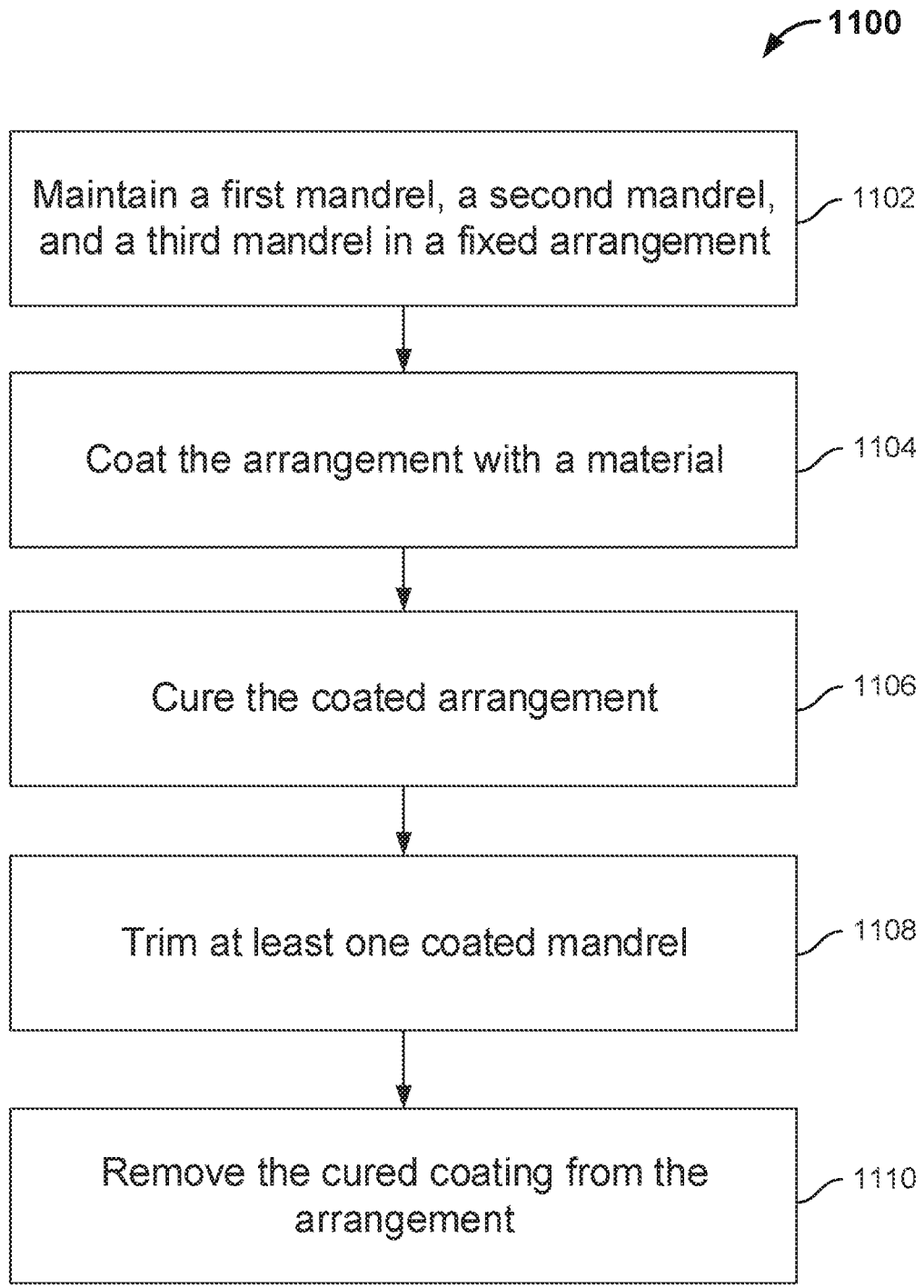
FIG. 11 shows a flowchart of an illustrative manufacturing process for a nosepiece of a nasal cannula.

FIG. 11 shows a flowchart of an illustrative manufacturing process for a nosepiece of a nasal cannula. Process 1100 begins at step 1102 where a first mandrel, a second mandrel, and a third mandrel are maintained in a fixed arrangement. The third mandrel is positioned between the first and second mandrels in close proximity. The third mandrel is held at a distance from the first and second mandrels. The mandrels may be made of, for example, steel, aluminum-bronze alloys, stainless steel, or any other suitable material, such as those resistance to curing methods and which will not permanently adhere to the flexible material used in forming the nosepiece. The process continues from step 1102 to step 1104 where the arrangement is coated with a material. For example, the material may be, polyvinyl chloride (PVC) plastic, plastisol, vinyl, silicone, non-latex rubber, an elastomer, ethylene vinyl acetate (EVA), styrene-butadiene copolymer (SBC), polyether ether ketone (PEEK), a polyether block amide (such as PEBAX), a polyethylene material, a high-density polyethylene (HDPE) material, a medium-density polyethylene (MDPE) material, a low-density polyethylene (LDPE) material, a crack-resistant material, a material with a low coefficient of friction, a material less than 70 Durometer Shore A, or any other suitable material). The process continues from step 1104 to step 1106, where the coated arrangement is cured. For example, the coated arrangement may be cured at room temperature or at a temperature or set of temperatures determined to accelerate the curing time. For example, the coating may be cured using a heat lamp, oven, UV radiation, or any other suitable means. The process continues from step 1106 to step 1108 where at least one coated mandrel is trimmed to create an opening in the coating of the trimmed mandrel. For example, the third mandrel may be a "sacrificial" mandrel, as described above. The coated third mandrel may be trimmed to allow the cured coating to be removed from the arrangement. The process continues from step 1108 to step 1110 where the cured coating is removed from the arrangement. For example, the cured coating may be a flexible plastic that is in the shape of the nosepiece shown in FIG. 1. The remaining excess material formed on the remaining untrimmed mandrels or all mandrels may then be trimmed.

In a bifurcated cannula, such as that described above in relation to FIG. 3, gas flow cannot split across a bridge between the two lumens. Because the two lumens split the total gas flow and are completely separate (e.g., not in fluid communication with one another), occluding one lumen will divert all flow through the other, non-occluded lumen. Occlusions may occur due to an obstruction, momentary kinking of the lumen, crushing the lumen by rolling over onto the tubing during sleep, or any other suitable occlusion. If the total gas flow through the system is maintained as a constant, when one lumen is occluded, the entire gas flow is directed to the other, non-occluded lumen, effectively doubling the flow rate delivered to the patient from that prong of the cannula. In many cases, the flow rate through a system is set to the maximum that is comfortable for the patient. The limiting factor for this is often the sensation of high velocity flow in the patient's nares. For this reason, doubling the flow is likely to be unpleasant for the patient.

Figure 12A:
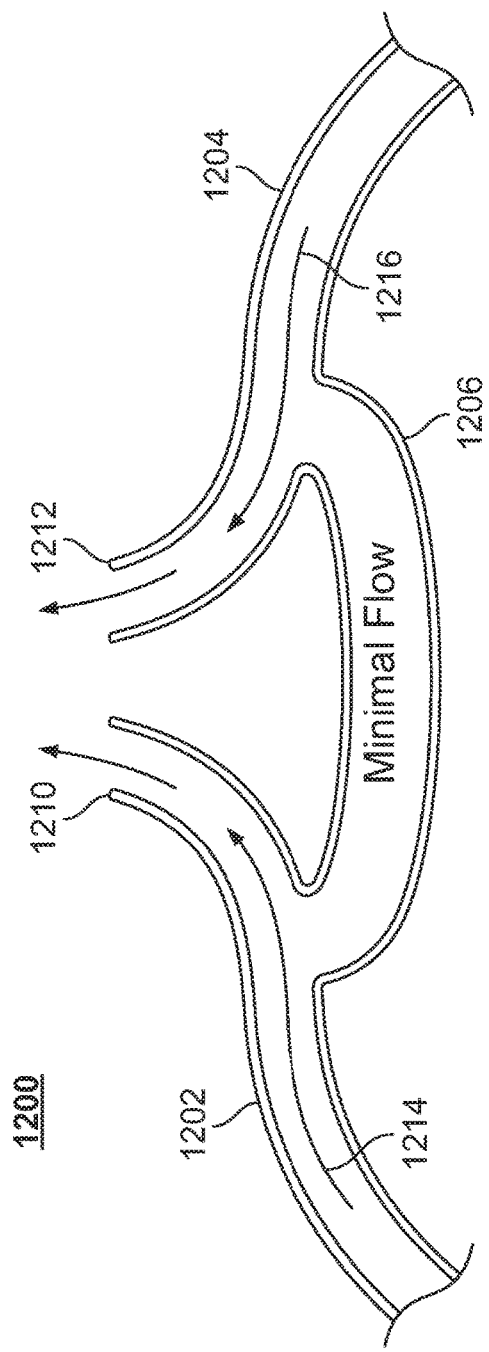
FIGS. 12A-12B show an illustrative nosepiece of a nasal cannula for respiratory therapy, with and without an occlusion, according to a further embodiment of the present disclosure.
Figure 12B:
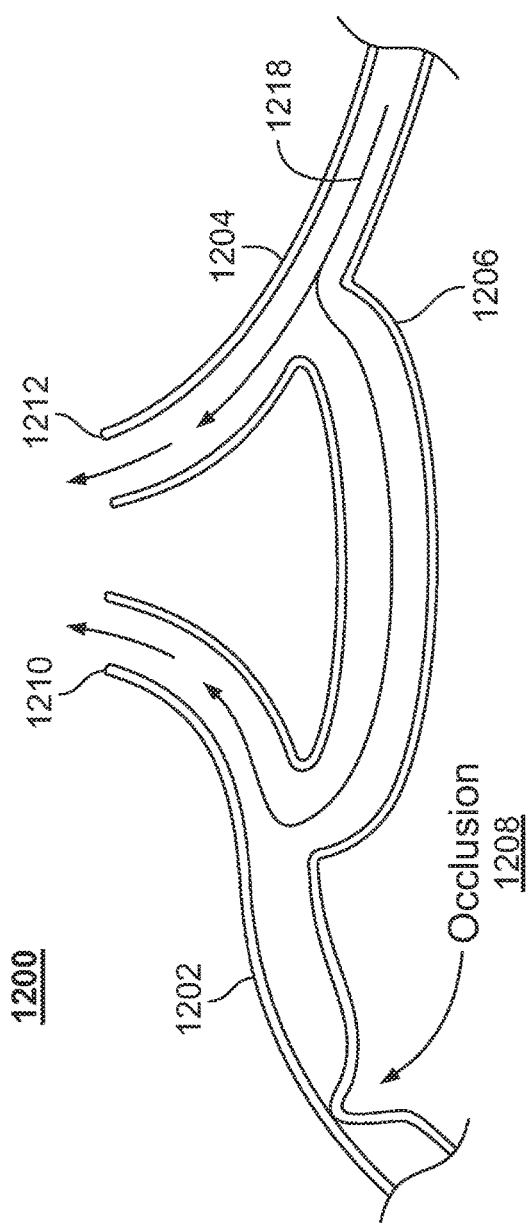

FIGS. 12A-12B show an illustrative non-bifurcated nosepiece during operation of a respiratory therapy system. FIG. 12A shows "normal" flow during operation. FIG. 12B shows flow during operation when a portion of the nosepiece is occluded. During normal operation as shown in FIG. 12A, air flow 1214 flows through first lumen 1202 and exits outlet end 1210. Air flow 1216 flows through second lumen 1204 and exits outlet end 1212. Little to now air flow travels through bridge 1206. If however, one of the first and second lumens is occluded, as shown in FIG. 12B, a large portion of air flow will flow through bridge 1206. In FIG. 12B first lumen 1202 is effectively blocked at occlusion 1208 such that little to no gas flow can pass through first lumen 1202 from one side of occlusion 1208 to the other side of occlusion 1208. Occlusions may include, but are not limited to, a bend in the tubing forming a lumen (e.g., if the tubing is bent at a sharp angle), pressure applied to the lumen externally (e.g., if the tubing is pinched), debris or other elements blocking the lumen internally, or any other occlusion that obstructs the flow of gas through a lumen 1202, 1204 in the nosepiece 1200. Due to occlusion 1208, gas flow 1218 flowing through second lumen 1204 splits off—a portion of gas flow 1218 exits second lumen 1204 through outlet end 1212, while a portion of gas flow 1218 flows through bridge 1206, into first lumen 1202, and exits via outlet end 1210. Thus, in non-bifurcated nosepieces such as nosepiece 1200, the nosepiece effectively self corrects if one of the two lumens is occluded—i.e., even if gas flow cannot pass through the entirety of one lumen (e.g., first lumen 1202), gas flow will still exit the outlet ends (e.g., outlet ends 1210, 1212) of both lumens (e.g., lumens 1202, 1204) because gas flow can pass through a bridge (e.g., bridge 1206) between the two lumens. A patient will therefore still receive gas from both outlet ends (that, in many cases, are placed within the patient's nares during operation of the system) even if one of the lumens is occluded.

Figure 13:
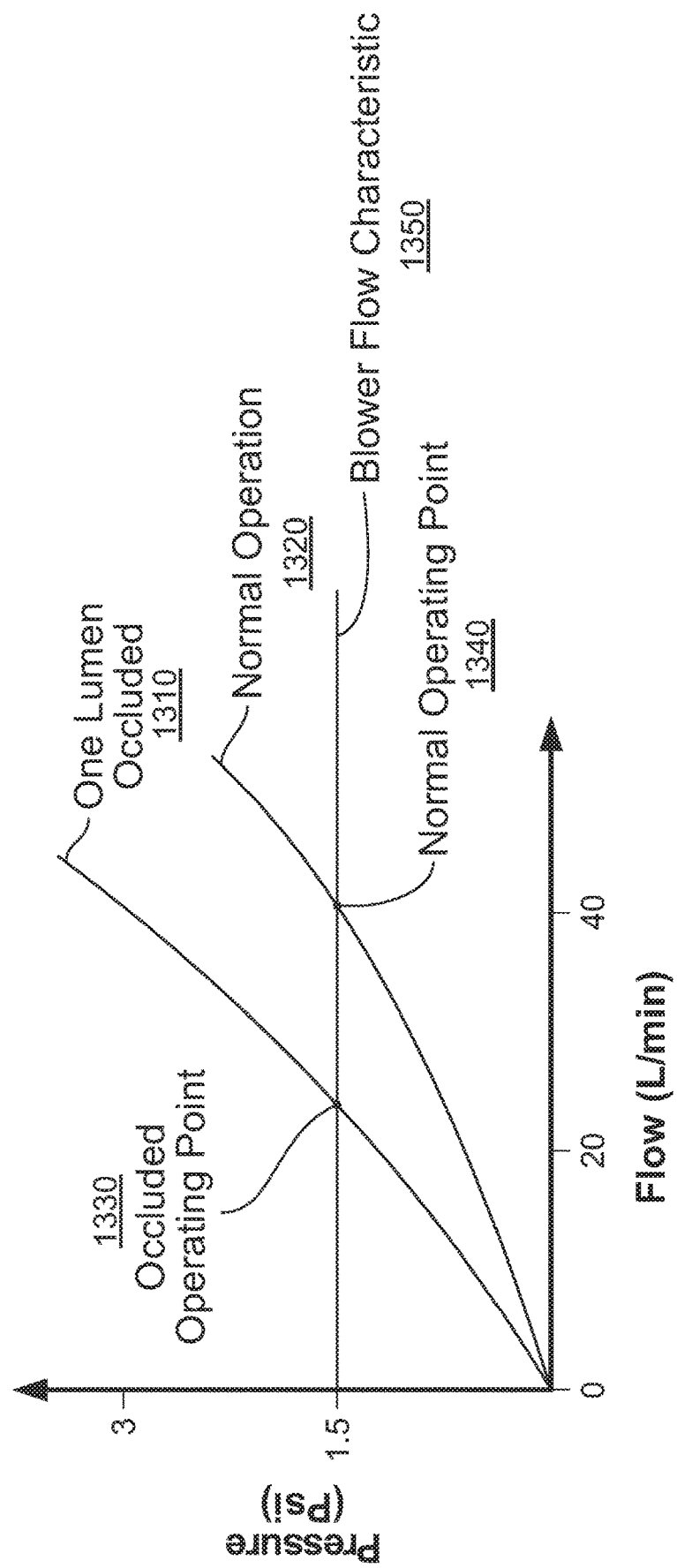
FIG. 13 shows an illustrative lumen pressure versus flowrate plot for the nasal cannula of FIGS. 12A-12B.

In a bifurcated cannula, such as that described above in relation to FIG. 3, however, gas flow cannot split across a bridge (e.g., bridge 314) between the two lumens (e.g., first lumen 330 and second lumen 332), unlike in the nosepiece of FIGS. 12A-B described above. FIG. 13 shows a graph depicting how pressure varies with flow between normal and occluded operation in a bifurcated cannula nosepiece. Pressure in pounds per square inch (Psi) is shown along the y-axis and flow in liters per minute (L/min) is shown along the x-axis. Curve 1310 shows pressure and flow through the cannula when one of two lumens is occluded. Curve 1320 shows pressure and flow through the cannula when both lumens are operating under normal conditions (i.e., non-occluded). Blower flow characteristic line 1350 shows a constant pressure of 1.5 Psi. Occluded curve 1310 intersections blower flow characteristic line 1350 at occluded operating point 1330. Normal operation curve 1320 intersects blower flow characteristic line 1350 at normal operating point 1340. As evidenced in FIG. 13, when a single lumen is occluded (e.g., as shown by curve 1310) the flow at a given pressure (e.g., 1.5 Psi shown by blower flow characteristic line 1350) is significantly less the flow at that pressure under normal operating conditions (e.g., as shown by curve 1320). In some implementations, a system may be configured to provide a constant flow. To maintain a constant flow, when one lumen is occluded, the pressure of the system would have to significantly increase. For example, if the system is set to maintain a flow rate of 40 L/min, when one lumen becomes occluded, the pressure necessary to maintain that flow rate would increase from 1.5 Psi to approximately 3 Psi.

There are multiple solutions to resolve this problem of reduced patient comfort resulting from occlusions in bifurcated cannulas. Such solutions include a flow feedback loop, an inherent flow limitation, a pressure feedback loop, a balancing shunt, or any suitable system or modification.

To prevent occlusions from inhibiting a patient's comfort, a flow feedback loop may be used. In the flow feedback loop, a desired flow rate is selected and set. In some implementations, the flow rate may be set by a clinician, a patient, an automated process, or any other suitable means. The respiratory therapy system monitors the back pressure required to deliver the set flow rate for a period of time. For example, the respiratory therapy system may include a sensor and processor configured to monitor back pressure and adjust the delivered flow rate. By monitoring the back pressure, the system establishes a benchmark for a non-occluded cannula—i.e., a cannula with two lumens where gas can flow through both lumens. The system maintains the current flow rate to the extent possible within a range of acceptable pressures around the benchmark. If the system requires more pressure than that acceptable pressure range allows to maintain the set flow rate, the system may trigger an alarm indicating the possibility of a partial occlusion. The system may also limit the flow rate to avoid causing discomfort to the patient.

To prevent occlusions from inhibiting a patient's comfort, an inherent flow limitation may be implemented. In this implementation, no feedback is required. A flow generator delivers a constant pressure at a particular input (operating rotations per minute) would be used. For example, the flow generator may be a standard blower system, and the speed of the blower may be the input. If the speed is maintained at a constant value, the pressure will also remain substantially constant at low flow rates (i.e., flow rates that require the blower to operate very close to the maximum pressure the blower can deliver when fully occluded). A desired flow rate is selected and set (e.g., by a clinician). The system then delivers a constant pressure output. An occlusion in a lumen would result in a decreased flow rate. The system monitors and detects the reduced flow rate and triggers an alarm (e.g., to notify a clinician of the reduced flow rate).

To prevent occlusions from inhibiting a patient's comfort, a pressure feedback loop may be implemented. A desired flow rate is selected and set (e.g., by a clinician). The system monitors the back pressure required to deliver this set flow rate for a period of time to establish a target pressure for a non-occluded cannula. The system maintains the pressure as a constant. If the flow rate deviates from the targeted flow set point, the system triggers an alarm indicating the possibility of a partial occlusion.

To prevent occlusions from inhibiting a patient's comfort, a balancing shunt may be implemented. A modification to the bifurcated cannula approach is to use a balancing shunt in the nosepiece. The shunt may comprise a flow path that connects the separate lumens in an area adjacent to the cannula prongs. The flow passage is configured so that in normal, non-occluded conditions, the pressure at both ends of the shunt (i.e., at the connection between the shunt and the lumens) are equal and net flow will pass through the shunt. If one of the lumens is occluded, however, the resulting pressure differential between the two lumens would cause flow through the shunt to balance the flow between the two prongs. In some implementations, the shunt is disposed in a location where the openings from the two lumens into the shunt do not disturb the flow in the lumens. For example, the shut may be located on a point tangent to the flow in the lumen and away from bends in the lumen.

The foregoing is merely illustrative of the principles of the disclosure, and the apparatuses can be practiced by other than the described implementations, which are presented for purposes of illustration and not of limitation. It is to be understood that the apparatuses disclosed herein, while shown for use in high flow therapy systems, may be applied to systems to be used in other ventilation circuits.

Variations and modifications will occur to those of skill in the art after reviewing this disclosure. The disclosed features may be implemented, in any combination and subcombination (including multiple dependent combinations and subcombinations), with one or more other features described herein. The various features described or illustrated above, including any components thereof, may be combined or integrated in other systems. Moreover, certain features may be omitted or not implemented.

Examples of changes, substitutions, and alterations are ascertainable by one skilled in the art and could be made without departing from the scope of the information disclosed herein. All references cited herein are incorporated by reference in their entirety and made part of this application.

What is claimed:

1. A system for respiratory therapy, the system comprising:
    (i) a nosepiece portion comprising:
        a first lumen comprising a first inlet end to receive a first flow of breathing gas, a first outlet end to deliver the first flow, and a first bend between the first inlet end and the first outlet end;
        a second lumen comprising a second inlet end to receive a second flow of breathing gas, a second outlet end to deliver the second flow, and a second bend between the second inlet end and the second outlet end; and
        a hollow bridge, having at least one opening, separating the first lumen and the second lumen, the bridge attaching to the first lumen and the second lumen;
        wherein the bridge forms a fluid conduit between the first lumen and the second lumen and
        wherein the bridge comprises a first opening along the base of the bridge, the first opening configured to couple a nebulizer to the nosepiece portion;
    (ii) a third elongated lumen, the third elongated lumen having an inlet end and an outlet end;
    (iii) a fourth elongated lumen, the fourth elongated lumen having an inlet end and an outlet end; and
    (iv) a source of breathing gas connected to the inlet ends of the third and fourth elongated lumens, wherein the nosepiece portion is configured to be connected to the outlet ends of the third and fourth elongated lumens.

2. The system of claim 1, wherein the bridge attaches to an outer surface of the first lumen at the first bend and an outer surface of the second lumen at the second bend.

3. The system of claim 2, wherein a material of the outer surfaces of the first and second lumens comprises at least one of: polyvinyl chloride (PVC) plastic, plastisol, vinyl, silicone, non-latex rubber, an elastomer, ethylene vinyl acetate (EVA), styrene-butadiene copolymer (SBC), polyether ether ketone (PEEK), a polyether block amide (such as PEBAX), a polyethylene material, a high-density polyethylene (HDPE) material, a medium-density polyethylene (MDPE) material, a low-density polyethylene (LDPE) material, a crack-resistant material, a material with a low coefficient of friction, a material less than 70 Durometer Shore A, and a flexible plastic.

4. The system of claim 1, wherein the breathing gas is humidified and heated.

5. The system of claim 1,
    wherein the third elongated lumen and the nosepiece portion define a constant diameter flow path for the first flow of breathing gas from the inlet end of the third elongated lumen to the outlet end of the first lumen; and
    wherein the fourth elongated lumen and the nosepiece portion define a constant diameter flow path for the second flow of breathing gas from the inlet end of the fourth elongated lumen to the outlet end of the second lumen.

6. The system of claim 5,
    wherein the first inlet end of the first lumen is adapted to be connected to the outlet end of the third elongated lumen without constricting the internal diameter of the third elongated lumen; and
    wherein the second inlet end of the second lumen is adapted to be connected to the outlet end of the fourth elongated lumen without constricting the internal diameter of the fourth elongated lumen.

7. The system of claim 1, comprising:
    a sensor and a processor configured to monitor back pressure.

8. The system of claim 7, wherein the system is configured to maintain a constant pressure and, if a flow rate deviates from a targeted flow set point, trigger an alarm indicating a possibility of a partial occlusion.

9. The system of claim 1, wherein the bridge is configured such that if one of the first or second lumens is occluded, a resulting pressure differential between the two lumens causes flow through the bridge to balance the flow between the two lumens.

* * * * *